US009558549B2

(12) United States Patent
Ishikawa et al.

(10) Patent No.: US 9,558,549 B2
(45) Date of Patent: Jan. 31, 2017

(54) IMAGE PROCESSING APPARATUS, METHOD OF CONTROLLING THE SAME AND STORAGE MEDIUM

(75) Inventors: Ryo Ishikawa, Kawasaki (JP); Takaaki Endo, Urayasu (JP); Kiyohide Satoh, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 26 days.

(21) Appl. No.: 14/008,826

(22) PCT Filed: Apr. 4, 2012

(86) PCT No.: PCT/JP2012/059827
§ 371 (c)(1),
(2), (4) Date: Sep. 30, 2013

(87) PCT Pub. No.: WO2012/141184
PCT Pub. Date: Oct. 18, 2012

(65) Prior Publication Data
US 2014/0037168 A1    Feb. 6, 2014

(30) Foreign Application Priority Data

Apr. 13, 2011   (JP) ................. 2011-089536

(51) Int. Cl.
G06K 9/00       (2006.01)
G06T 7/00       (2006.01)
(Continued)

(52) U.S. Cl.
CPC ............. *G06T 7/0012* (2013.01); *A61B 5/055* (2013.01); *A61B 6/5247* (2013.01);
(Continued)

(58) Field of Classification Search
USPC ........ 382/100, 103, 106–107, 128–134, 154, 382/162, 168, 181, 199, 209, 219, 232, 382/254, 274, 276, 285–291, 305, 312; 600/443, 462; 378/4, 21; 345/441; 702/150
See application file for complete search history.

(56) References Cited

U.S. PATENT DOCUMENTS 8,165,372 B2    4/2012   Ishikawa et al. ............. 382/128
8,345,927 B2    1/2013   Ishikawa et al. ............. 382/106
(Continued)

FOREIGN PATENT DOCUMENTS

EP    2131326    12/2009
JP    3871747    1/2007
(Continued)

OTHER PUBLICATIONS

M.M.J. Letteboer et al., "Brain Shift Estimation in Image-Guided Neurosurgery Using 3-D Ultrasound", *IEEE Transactions on Biomedical Engineering*, vol. 52, No. 2 (Feb. 2005).
(Continued)

Primary Examiner — Seyed Azarian
(74) Attorney, Agent, or Firm — Fitzpatrick, Cella, Harper & Scinto

(57) ABSTRACT

An image processing apparatus comprises: shape obtaining means for obtaining information indicating a surface shape of a target object; discrimination means for discriminating a contact portion and a noncontact portion between the target object and an imaging surface of an ultrasonic probe which captures an ultrasonic image of the target object; position and orientation obtaining means for obtaining information indicating a position and orientation of the ultrasonic probe at the time of imaging; and alignment means for estimating deformation of the target object based on information indicating the surface shape, a discrimination result obtained by the discrimination means, and information indicating the
(Continued)

position and orientation, and aligning the surface shape with the ultrasonic image.

22 Claims, 17 Drawing Sheets

(51) Int. Cl.
    *A61B 5/055*     (2006.01)
    *A61B 6/00*     (2006.01)
    *A61B 8/00*     (2006.01)
    *A61B 8/14*     (2006.01)
    *A61B 8/08*     (2006.01)

(52) U.S. Cl.
    CPC .......... *A61B 8/4245* (2013.01); *A61B 8/4263* (2013.01); *A61B 8/486* (2013.01); *A61B 8/5261* (2013.01); *G06T 7/0028* (2013.01); *G06T 7/0083* (2013.01); *G06T 7/0089* (2013.01); *A61B 8/08* (2013.01); *A61B 8/429* (2013.01); *G06T 2207/10088* (2013.01); *G06T 2207/10132* (2013.01)

(56) References Cited

U.S. PATENT DOCUMENTS

| | | | | |
|---|---|---|---|---|
| 2007/0167784 | A1 | 7/2007 | Shekhar et al. | 600/427 |
| 2008/0300487 | A1* | 12/2008 | Govari | A61B 8/4254 600/443 |
| 2009/0326373 | A1 | 12/2009 | Boese et al. | 600/427 |
| 2010/0239150 | A1* | 9/2010 | Ishikawa | A61B 5/0095 382/131 |
| 2011/0142308 | A1* | 6/2011 | Ishikawa | G06T 3/0093 382/128 |
| 2011/0246129 | A1* | 10/2011 | Ishikawa | A61B 8/00 702/150 |
| 2011/0262015 | A1 | 10/2011 | Ishikawa et al. | 382/128 |
| 2012/0262460 | A1* | 10/2012 | Endo | A61B 5/055 345/441 |
| 2013/0188851 | A1 | 7/2013 | Miyasa et al. | 382/131 |
| 2013/0195339 | A1 | 8/2013 | Endo et al. | 382/131 |
| 2014/0023254 | A1 | 1/2014 | Ishikawa et al. | 382/131 |

FOREIGN PATENT DOCUMENTS

| | | |
|---|---|---|
| JP | 2010-131269 | 6/2010 |
| JP | A 2010-131269 | 6/2010 |

OTHER PUBLICATIONS

W. Wein et al., "Automatic Registration and Fusion of Ultrasound with CT to Radiotherapy", *Proc. MICCAI 2005*, vol. 2, pp. 303-311 (2005).

W. Wein et al., "Integrating Diagnostic B-Mode Ultrasonography Into CT-Based Radiation Treated Planning", *IEEE Transactions on Medical Imaging*, vol. 26, No. 6 (Jun. 2007).

* cited by examiner

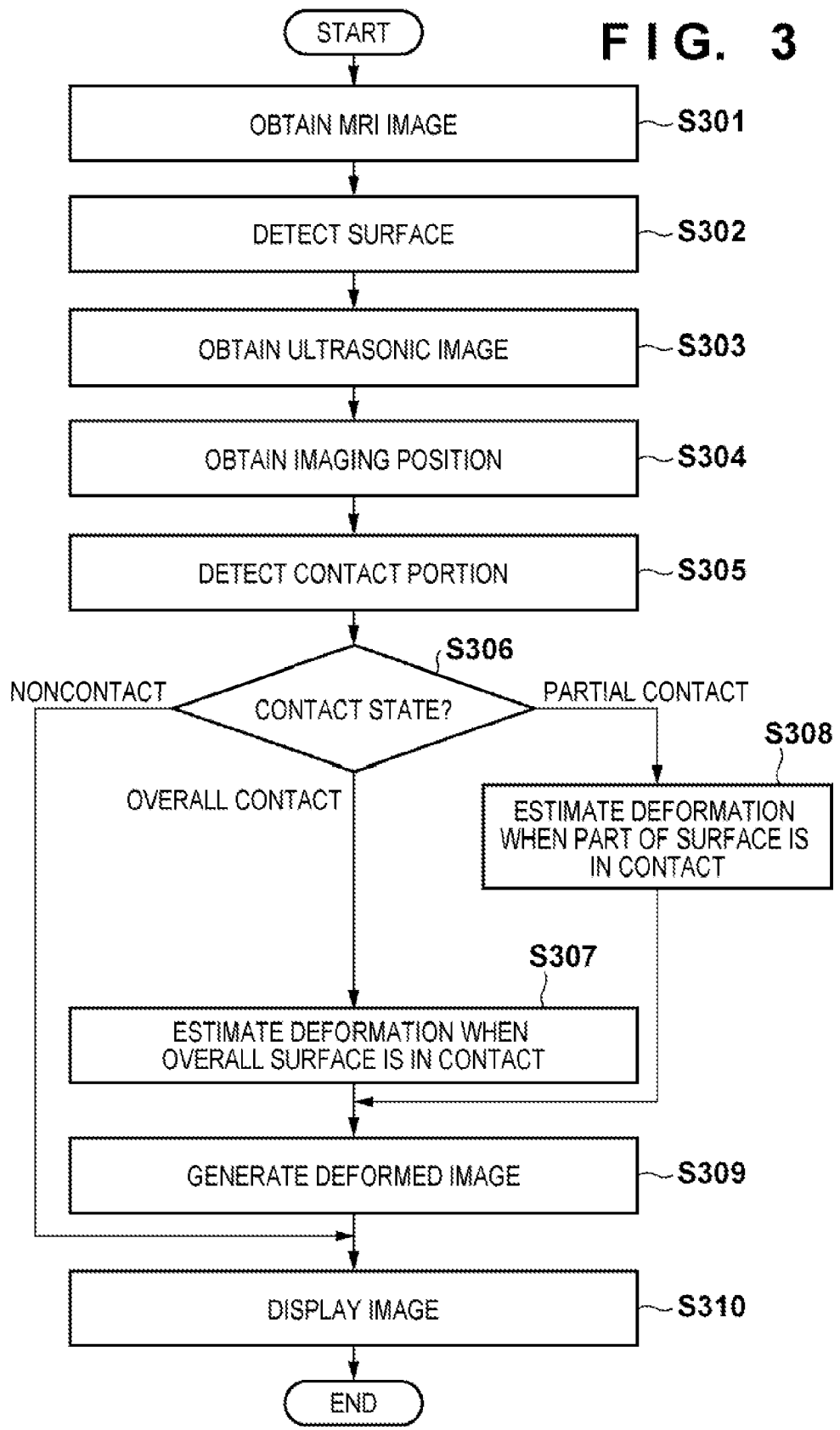

F I G. 11
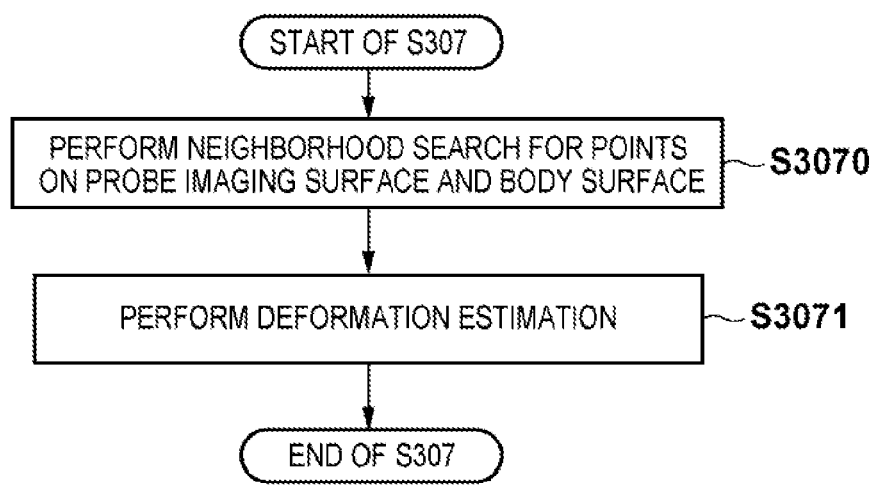

F I G. 14A
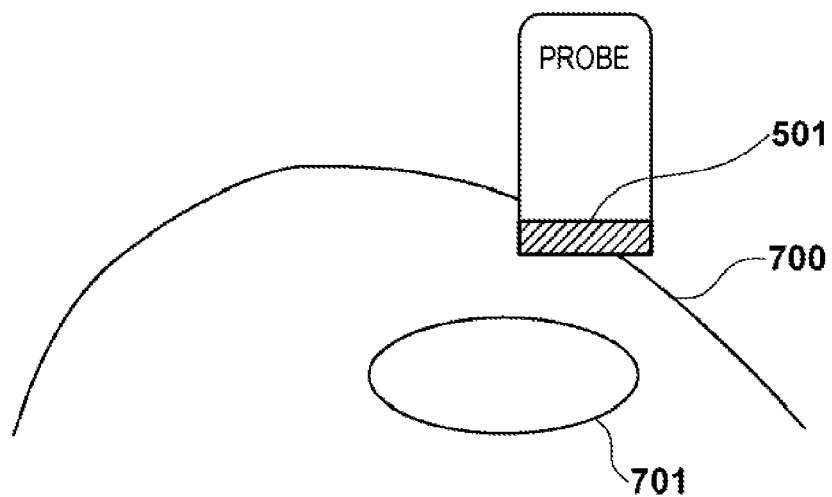
F I G. 14B
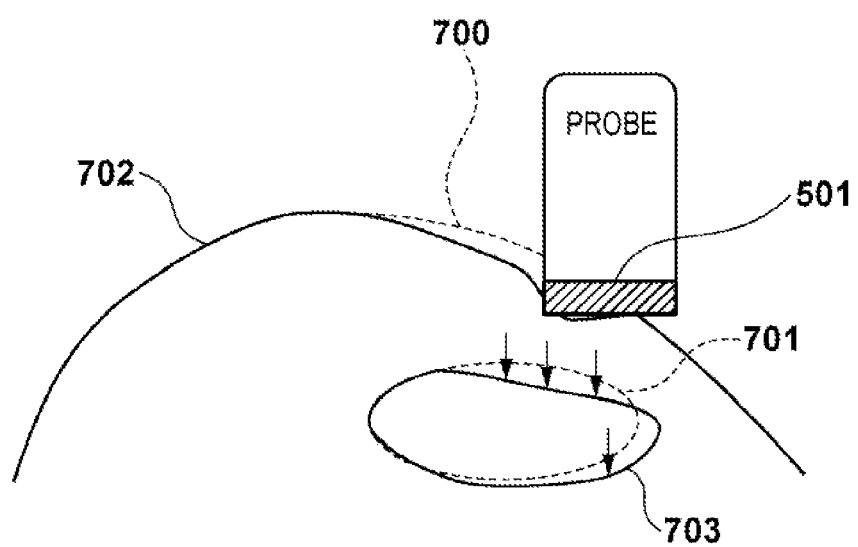

IMAGE PROCESSING APPARATUS, METHOD OF CONTROLLING THE SAME AND STORAGE MEDIUM

TECHNICAL FIELD

The present invention relates to an image processing apparatus, a method of controlling the same, and a storage medium and, more particularly, to an image processing apparatus which processes medical images captured by various types of medical image obtaining apparatuses (modalities) such as an X-ray computed tomography apparatus (X-ray CT), magnetic resonance imaging apparatus (MRI), nuclear medicine diagnostic apparatus (SPECT or PET), and ultrasonic image diagnostic apparatus, a method of controlling the image processing apparatus, and a storage medium.

BACKGROUND ART

In the medical field, a doctor displays the medical images obtained by imaging a patient on a monitor, interprets the displayed medical images, and observes the state of a morbid portion and temporal changes in it. Apparatuses which generate this type of medical images include, for example, an X-ray imaging apparatus, X-ray computed tomography apparatus (X-ray CT), magnetic resonance imaging apparatus (MRI), nuclear medicine diagnostic apparatus (SPECT or PET), and ultrasonic image diagnostic apparatus (US). In image diagnosis in which a doctor diagnoses a patient by using the images obtained from such apparatuses which generate medical images, the doctor selects proper apparatuses depending on the region or disease to be diagnosed in consideration of the differences in characteristic between the apparatuses. In some case, a doctor performs diagnosis by using a plurality of images obtained from a plurality of apparatuses in order to improve the accuracy of the diagnosis. For example, it is possible to obtain information more effective for diagnosis by imaging the same object using both an ultrasonic image diagnostic apparatus and an MRI and using a combination of the captured images.

When performing diagnosis using a combination of ultrasonic images and MRI images, it is effective to perform diagnosis upon associating corresponding regions between two images. For this purpose, it is necessary to perform alignment between the two images. In order to implement this, there are several problems to be solved. The first problem is that since a doctor or technician images an object to be examined while holding an imaging probe (to be referred to as a "probe" hereinafter) and freely moving it, the correspondence between a position in a space with reference to the object and a captured image is not clear. The second problem is that an image captured as an ultrasonic image is generally a two-dimensional tomogram of the inside of an object to be examined, and hence differs in the spatial dimension of information which can be obtained from an MRI image obtained by capturing three-dimensional information.

One of the approaches to these problems is a method of measuring the position and orientation of a probe by using an external sensor. Japanese Patent No. 03871747 discloses a technique of obtaining a slice image corresponding to a region imaged by an ultrasonic image diagnostic apparatus from a three-dimensional medical image, captured in advance, in accordance with the measurement value from a device for measuring a position and orientation which is mounted on the probe, and displaying the images side by side. This technique allows to observe an ultrasonic image of a two-dimensional slice in association with three-dimensional information obtained by another modality.

Studies have been made to align these two modalities by using the image information of an ultrasonic image and three-dimensional medical image. The technique disclosed in W. Wein, B. Roper, and N. Navab, "Automatic registration and fusion of ultrasound with CT to radiotherapy", Proc. MICCAI 2005, vol. 2, pp. 303-311, 2005 generates an ultrasonic simulation image based on a three-dimensional medical image obtained in advance. This technique associates an ultrasonic image actually captured by an ultrasonic image diagnostic apparatus with a simulation image based on image information.

Japanese Patent Laid-Open No. 2010-131269 discloses a technique of improving the processing efficiency by obtaining a surface shape of an object from a three-dimensional medical image, and limiting a search range for association by associating images under conditions that make the positions of the surface shape and the imaging surface of a probe match, based on the positions of the surface shape and imaging surface of the probe.

According to the technique disclosed in Japanese Patent No. 03871747, it is difficult to accurately align an ultrasonic image with a three-dimensional medical image when the accuracy of a sensor is insufficient. In addition, even with the use of a high-accuracy position and orientation sensor, if an imaging region deforms due to the body movement of an object or the pressing force of the probe, it is also difficult to accurately perform alignment. On the other hand, the technique disclosed in W. Wein, B. Roper, and N. Navab, "Automatic registration and fusion of ultrasound with CT to radiotherapy", Proc. MICCAI 2005, vol. 2, pp. 303-311, 2005 can perform accurate alignment including the correction of the above deformation by performing alignment processing between an ultrasonic image and an MRI image based on image information. However, since this technique requires a very large amount of calculation, it is difficult to perform alignment at high speed. This impairs the synchronization between imaging and observation. In addition, since the technique disclosed in Japanese Patent Laid-Open No. 2010-131269 performs processing on the assumption that the overall imaging surface of the probe is in contact with an object, when the probe is in contact with only part of the object, the accuracy of an alignment result deteriorates.

SUMMARY OF INVENTION

In consideration of the above problems, the present invention provides a technique of aligning an ultrasonic image with a three-dimensional medical image with high accuracy at high speed.

According to one aspect of the present invention, there is provided an image processing apparatus comprising: shape obtaining means for obtaining information indicating a surface shape of a target object; discrimination means for discriminating a contact portion and a noncontact portion between the target object and an imaging surface of an ultrasonic probe which captures an ultrasonic image of the target object; position and orientation obtaining means for obtaining information indicating a position and orientation of the ultrasonic probe at the time of imaging; and alignment means for estimating deformation of the target object based on information indicating the surface shape, a discrimination result obtained by the discrimination means, and information indicating the position and orientation, and aligning the surface shape with the ultrasonic image.

According to one aspect of the present invention, there is provided a method of controlling an image processing apparatus including shape obtaining means, discrimination means, position and orientation obtaining means, and alignment means, the method comprising: a shape obtaining step of causing the shape obtaining means to obtain information indicating a surface shape of a target object; a discrimination step of causing the discrimination means to discriminate a contact portion and a noncontact portion between the target object and an imaging surface of an ultrasonic probe which captures an ultrasonic image of the target object; a position and orientation obtaining step of causing the position and orientation obtaining means to obtain information indicating a position and orientation of the ultrasonic probe at the time of imaging; and an alignment step of causing the alignment means to estimate deformation of the target object based on information indicating the surface shape, a discrimination result obtained in the discrimination step, and information indicating the position and orientation, and align the surface shape with the ultrasonic image.

Further features of the present invention will be apparent from the following description of exemplary embodiments with reference to the attached drawings.

BRIEF DESCRIPTION OF DRAWINGS

FIG. 3 is a flowchart showing a processing procedure in an image processing apparatus 100;

FIG. 11 is a flowchart showing the details of a processing procedure in step S307 in FIG. 3;

FIGS. 14A and 14B are views for explaining processing in step S308 in FIG. 3;

DESCRIPTION OF EMBODIMENTS

An exemplary embodiment(s) of the present invention will now be described in detail with reference to the drawings. It should be noted that the relative arrangement of the components, the numerical expressions and numerical values set forth in these embodiments do not limit the scope of the present invention unless it is specifically stated otherwise.

First Embodiment

Figure 1:
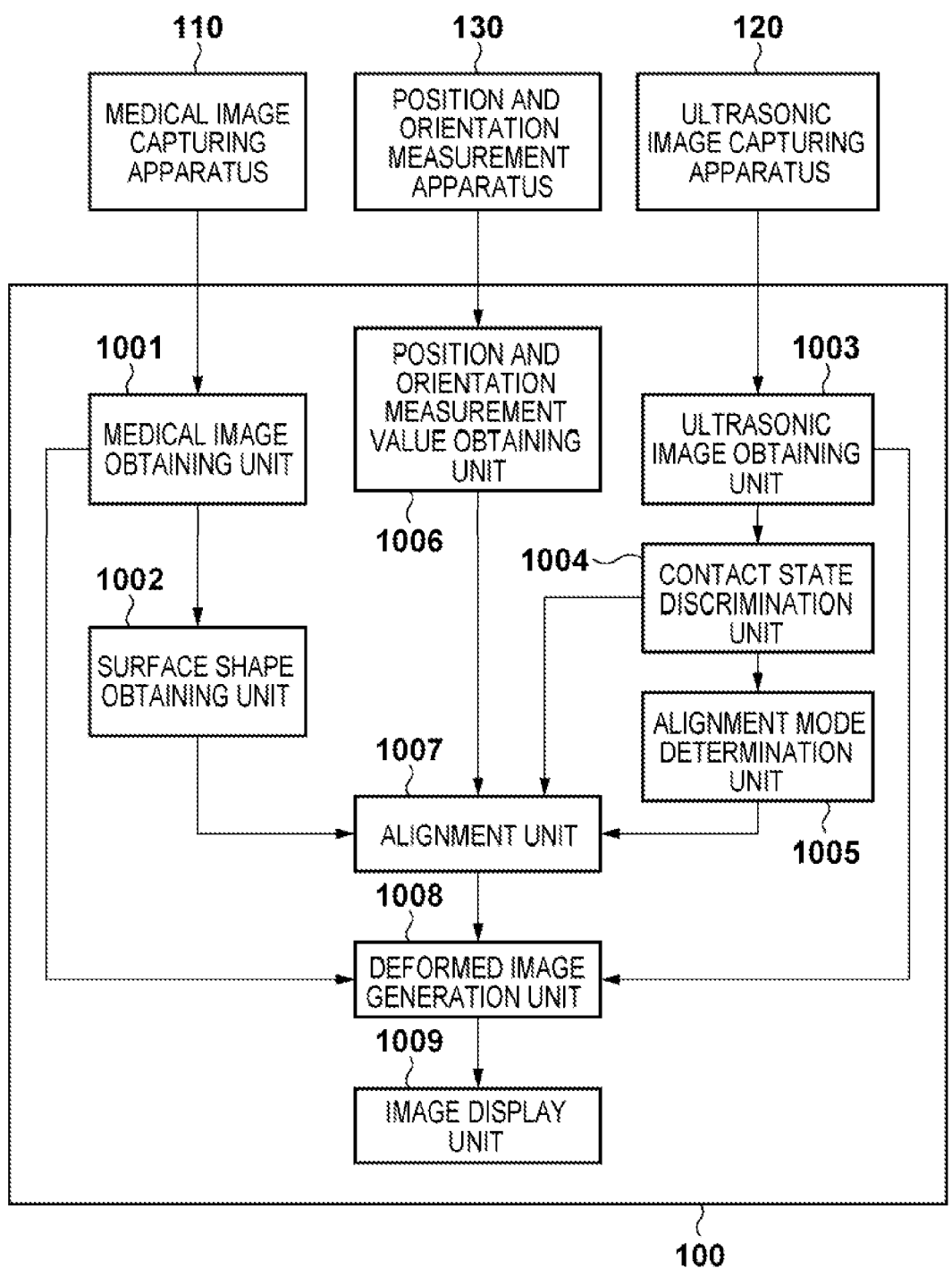
FIG. 1 is a block diagram showing the functional arrangement of an image processing system.

FIG. 1 is a block diagram showing the functional arrangement of an image processing system according to this embodiment. An image processing apparatus 100 is connected to a medical image capturing apparatus 110, an ultrasonic image capturing apparatus 120, a position and orientation measurement apparatus 130. The medical image capturing apparatus 110 is, for example, an MRI, which obtains a three-dimensional MRI image by imaging a predetermined three-dimensional region of an object to be examined. Assume that the ultrasonic image capturing apparatus 120 obtains a two-dimensional B-mode ultrasonic image by imaging a predetermined two-dimensional region of an object by ultrasonically imaging the inside of the object upon bringing an ultrasonic probe (not shown), which transmits and receives ultrasonic waves used for ultrasonic imaging, into contact with the object.

The position and orientation measurement apparatus 130 measures the position and orientation of the ultrasonic probe (not shown) of the ultrasonic image capturing apparatus 120. The position and orientation measurement apparatus 130 includes, for example, a magnetic transmission unit (not shown) and a magnetic reception unit (not shown). The magnetic transmission unit is fixed in a space in which measurement is performed, and transmits magnetic signals. The magnetic reception unit receives magnetic signals. The position and orientation measurement apparatus 130 measures the relationship between the position and orientation of the magnetic transmission unit and those of the magnetic reception unit by processing the magnetic signal received by the magnetic reception unit. In this case, the position and orientation of the probe are measured in a coordinate system with reference to the magnetic transmission unit by fixing the probe to the magnetic reception unit.

The image processing apparatus 100 performs alignment processing between the MRI image captured by the medical image capturing apparatus 110 and the ultrasonic image captured by the ultrasonic image capturing apparatus 120 based on the MRI image, the ultrasonic image, and the position and orientation of the probe measured by the position and orientation measurement apparatus 130.

The image processing apparatus 100 includes a medical image obtaining unit 1001, a surface shape obtaining unit 1002, an ultrasonic image obtaining unit 1003, a contact state discrimination unit 1004, an alignment mode determination unit 1005, a position and orientation measurement value obtaining unit 1006, an alignment unit 1007, a deformed image generation unit 1008, and an image display unit 1009.

The medical image obtaining unit 1001 obtains an MRI image of an object imaged by the medical image capturing apparatus 110, and transmits the resultant data to the surface shape obtaining unit 1002 and the deformed image generation unit 1008. The surface shape obtaining unit 1002 detects the position of each pixel corresponding to a surface of the object by processing the MRI image, and generates information about the shape of the surface (surface shape) as a set of positional coordinates of the pixels in the MRI image coordinate system. The resultant data is transmitted to the alignment unit 1007.

The ultrasonic image obtaining unit 1003 obtains an ultrasonic image of the object imaged by the ultrasonic image capturing apparatus 120, and transmits the resultant data to the contact state discrimination unit 1004 and the deformed image generation unit 1008. The contact state discrimination unit 1004 discriminates a contact portion and a noncontact portion between the probe imaging surface and the object by processing the obtained ultrasonic image, and transmits the result to the alignment mode determination unit 1005 and the alignment unit 1007.

The alignment mode determination unit 1005 determines a proper processing mode to be executed by the alignment unit 1007 (to be described later) based on the discrimination result from the contact state discrimination unit 1004, and transmits the result to the alignment unit 1007.

The position and orientation measurement value obtaining unit 1006 obtains a measurement result about the position and orientation of the probe which is output from the position and orientation measurement apparatus 130, and outputs the measurement result to the alignment unit 1007. The alignment unit 1007 estimates the deformation of the object between the MRI time and the ultrasonic imaging time based on the information obtained from each of the surface shape obtaining unit 1002, the position and orientation measurement value obtaining unit 1006, and the contact state discrimination unit 1004. The alignment unit 1007 then aligns the MRI image with the ultrasonic image based on the estimation, and transmits the resultant data to the deformed image generation unit 1008. Note that the alignment unit 1007 executes processing upon switching a plurality of different processing modes based on the processing result obtained by the alignment mode determination unit 1005.

The deformed image generation unit 1008 generates a deformed image by deforming either or both of the MRI image obtained by the medical image obtaining unit 1001 and the ultrasonic image obtained by the ultrasonic image obtaining unit 1003 based on the processing result obtained by the alignment unit 1007. The deformed image generation unit 1008 then transmits the result to the image display unit 1009. The image display unit 1009 executes the processing of displaying the deformed image generated by the deformed image generation unit 1008.

Figure 2:
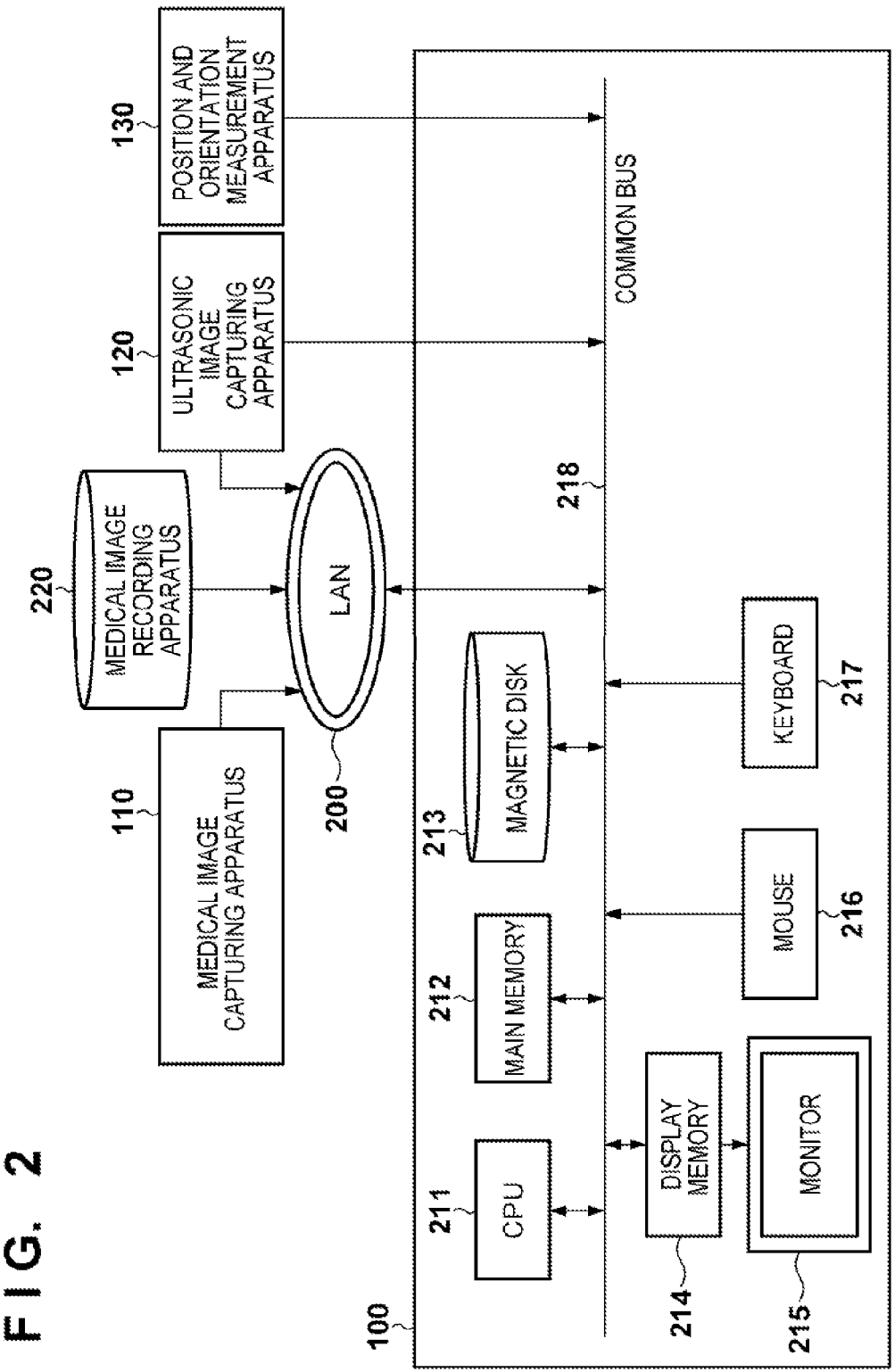
FIG. 2 is a block diagram showing the apparatus arrangement of an image processing system.

FIG. 2 is a block diagram showing the apparatus arrangement of the image processing system according to the first embodiment. The image processing system includes the image processing apparatus 100 and also includes the medical image capturing apparatus 110, a medical image recording apparatus 220, and the ultrasonic image capturing apparatus 120 via a local area network (LAN) 200, and the position and orientation measurement apparatus 130.

The image processing apparatus 100 can be implemented by, for example, a personal computer (PC). The image processing apparatus 100 includes a central processing unit (CPU) 211, a main memory 212, a magnetic disk 213, a display memory 214, a monitor 215, a mouse 216, and a keyboard 217.

The CPU 211 controls the operation of each constituent element of the image processing apparatus 100 described mainly with reference to FIG. 1. The main memory 212 stores a control program executed by the CPU 211, and provides a work area at the time of execution of a program by the CPU 211. The magnetic disk 213 stores an operating system (OS), device drives for peripheral devices, and various kinds of application software including a program for performing alignment processing (to be described later). The display memory 214 temporarily stores display data for the monitor 215. The monitor 215 is, for example, a CRT monitor or liquid crystal monitor, and displays an image based on data from the display memory 214. The user performs pointing input operation and inputs characters, commands, and the like by using the mouse 216 and the keyboard 217. These constituent elements are communicatively connected to each other via a common bus 218.

In this embodiment, the image processing apparatus 100 can read out and obtain medical image data from the medical image recording apparatus 220 via the LAN 200. In addition, it is possible to directly obtain medical image data or the like from the medical image capturing apparatus 110 via the LAN 200. However, the present invention is not limited to this. For example, external storage devices such as a USB memory may be connected to the image processing apparatus 100 to read out and obtain medical image data from the devices. In addition, the processing results obtained by this image processing system may be stored in these devices.

The image processing apparatus 100 is connected to the ultrasonic image capturing apparatus 120, and can obtain the ultrasonic images captured by the ultrasonic image capturing apparatus 120. In addition, the image processing apparatus 100 may record the ultrasonic images captured by the ultrasonic image capturing apparatus 120 on the medical image recording apparatus 220 and read out and obtain ultrasonic images from the medical image recording apparatus 220.

The overall processing operation performed by the image processing apparatus 100 will be described in detail next with reference to the flowchart of FIG. 3. This embodiment is implemented by making the CPU 211 execute programs which are stored in the main memory 212 and implement the functions of the respective units.

(Step S301): MRI Image Obtaining Processing

First of all, in step S301, the medical image obtaining unit 1001 obtains an MRI image by imaging an object by using the medical image capturing apparatus 110. This embodiment will exemplify a case in which an MRI image is three-dimensional image information. This image information is written as $I_{MRI}(x, y, z)$. In this case, $I_{MRI}(x, y, z)$ is a scalar function representing the luminance value of an MRI image at the position of a positional coordinate vector (x, y, z) in the MRI coordinate system. The obtained MRI image $I_{MRI}(x, y, z)$ is transmitted to the surface shape obtaining unit 1002 and the alignment unit 1007.

(Step S302): Surface Detection Processing

Figure 4A:
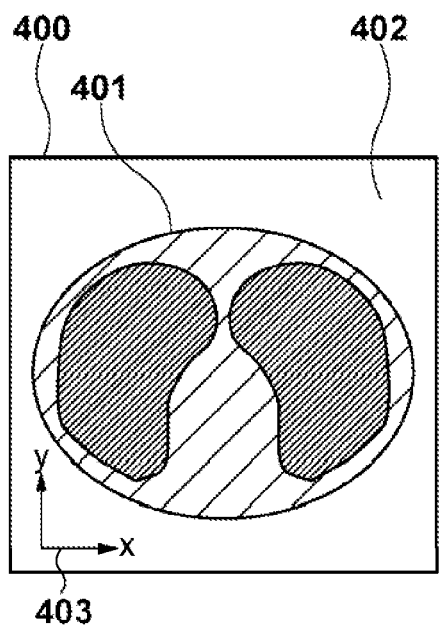
FIGS. 4A to 4C are views for explaining processing in step S302 in FIG. 3.
Figure 4B:
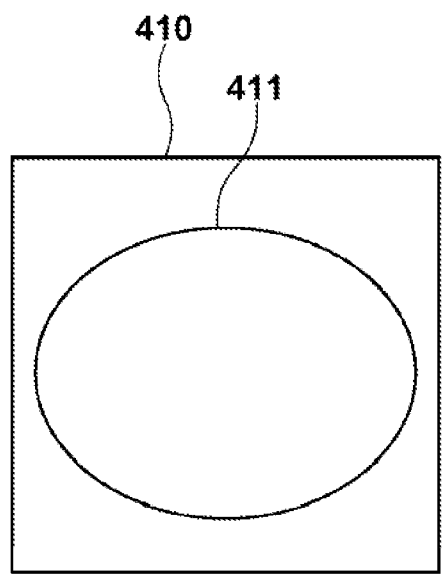

In step S302, the surface shape obtaining unit 1002 detects the position of each pixel (surface position) corresponding to a surface of the object from the medical image $I_{MRI}(x, y, z)$ obtained in step S301, and obtains a surface shape. This processing will be described with reference to FIGS. 4A to 4C. FIG. 4A is a schematic view showing a two-dimensional image for explaining the MRI image $I_{MRI}(x, y, z)$ obtained in step S301 on the drawing surface. Assume that the positions of the pixels constituting an MRI image 400 are defined in an MRI image coordinate system 403. The MRI image 400 depicts imaging results on both a region in an inside 401 of the object and a region of an outside 402 of the object. FIG. 4B shows a surface detection image 410 obtained by detecting a surface position 411 as the boundary between the inside 401 of the object and the outside 402 of the object from the MRI image 400 in FIG. 4A. This image is, for example, a binary image which allows to distinguish positions on the surface of the object from other positions. The surface shape obtaining unit 1002 detects the surface position 411 by processing the MRI image 400, and generates the surface detection image 410.

Figure 4C:
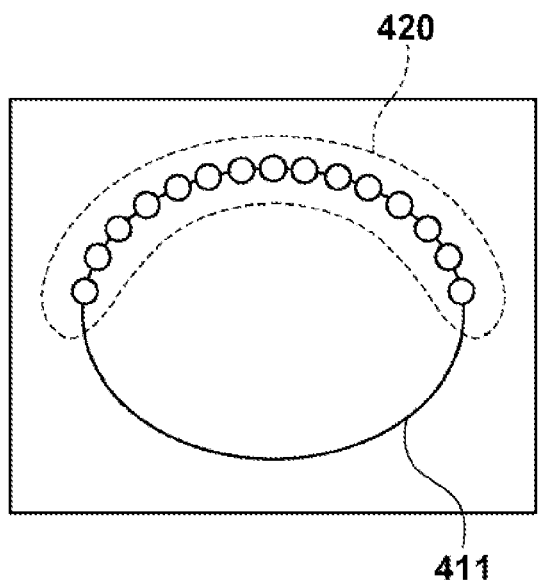

Various methods are conceivable as methods of detecting the surface position 411. For example, it is possible to detect a surface position by obtaining the spatial gradients of the luminance values of the MRI image 400 and performing threshold processing for the magnitudes of the spatial luminance gradients. The method of detecting the surface position 411 of the object is not limited to this, and any known method may be used. The surface shape obtaining unit 1002 further obtains surface points 420 from the pixels constituting the surface position 411, as shown in FIG. 4C, by processing the surface detection image 410. The surface shape obtaining unit 1002 may obtain the surface points 420 by, for example, obtaining points from the pixels constituting the surface position 411 at predetermined intervals or may obtain all the pixels constituting the surface position 411 as the surface points 420.

It is not always necessary to automatically obtain positions on the surface of an object by processing the MRI image 400. For example, it is possible to obtain the position or the like manually designated by the user using, for example, the mouse 216 or the keyboard 217 shown in FIG. 2.

This embodiment obtains the surface points 420 as the surface shape of the object, which is represented by $N_s$ points $S_i$ ($1 \leq i \leq N_s$), and records the positions of the points as three-dimensional positional coordinate vectors $x_{si}$ in the MRI image coordinate system 403. In the embodiment, the vectors are written as $x_{si} = (x_{si}, y_{si}, z_{si})^T$, ($1 \leq i \leq N_s$).

(Step S303): Ultrasonic Image Obtaining Processing

Figure 5:
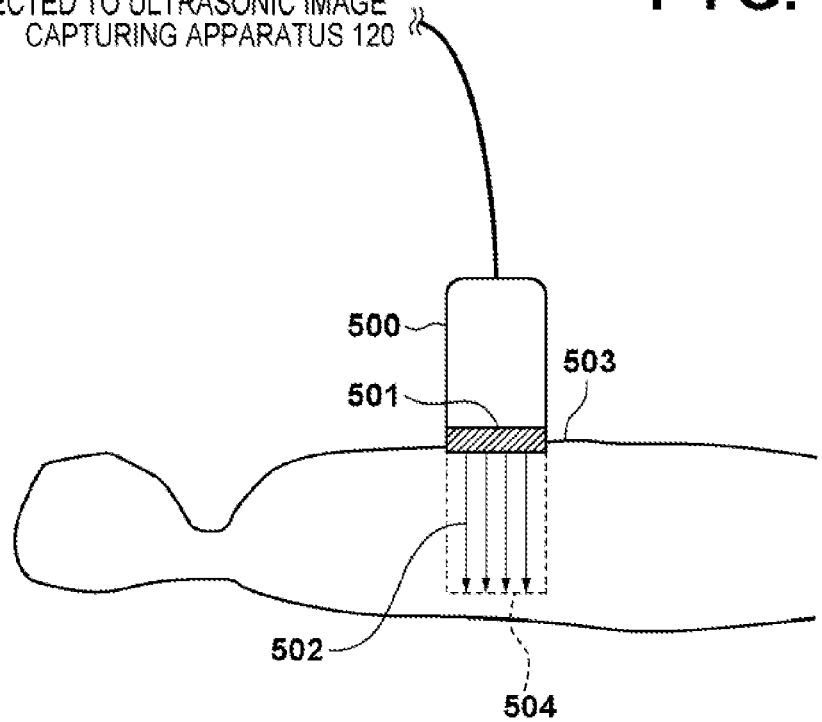
FIG. 5 is a view for explaining ultrasonic imaging.

In step S303, the ultrasonic image obtaining unit 1003 obtains the ultrasonic image captured by the ultrasonic image capturing apparatus 120 by imaging the object. This image may be directly obtained in synchronism with imaging by the ultrasonic image capturing apparatus 120. The ultrasonic image captured in the past by the ultrasonic image capturing apparatus 120 may be recorded on the medical image recording apparatus 220 in FIG. 2 and may be read out and input. An ultrasonic image may be a two-dimensional image or three-dimensional image or may be an ultrasonic image such as an elastogram. This embodiment will exemplify a case in which an ultrasonic image to be obtained is a two-dimensional B-mode tomogram of the object. FIG. 5 shows how the ultrasonic image capturing apparatus 120 captures an ultrasonic image of the object. Referring to FIG. 5, an ultrasonic probe 500 applies ultrasonic beams 502 from a probe imaging surface 501 to an ultrasonic imaging target region 504 and receives reflected beams under the control of the ultrasonic image capturing apparatus 120. At this time, when the probe imaging surface 501 is in contact with a surface 503 of the object, the ultrasonic beams 502 propagate inside the object, thereby ultrasonically imaging the inside of the object. When the probe imaging surface 501 is separate from the surface 503, since the ultrasonic beams 502 do not propagate inside the object, the inside of the object is not ultrasonically imaged.

Figure 6:
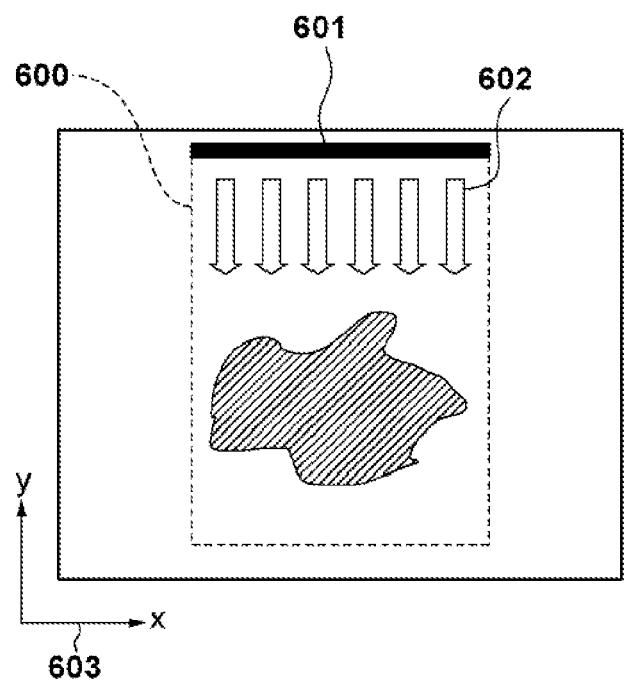
FIG. 6 is a view for explaining ultrasonic imaging in detail.

FIG. 6 shows an example of the ultrasonic image captured by the ultrasonic image capturing apparatus 120. In this case, an ultrasonic image is written as a scalar function $I_{US}$ (x, y, z) representing the luminance values of the ultrasonic image at the positions of positional coordinate vectors (x, y, z) in an ultrasonic image coordinate system 603. Note that when an ultrasonic image is a two-dimensional image, its image coordinates are represented by a two-dimensional coordinate system, and the positional coordinate vectors (x, y, z) can be reread as (x, y). However, in this embodiment configured to perform alignment with a three-dimensional MRI image, for the sake of convenience, an ultrasonic image coordinate system is a three-dimensional coordinate system (x, y, z), and it is interpreted that image information exists on a plane represented by z=0. Referring to FIG. 6, the ultrasonic probe 500 shown in FIG. 5 applies the ultrasonic beams 502 to an imaging region 600. The ultrasonic image of the inside of the object which is obtained by receiving reflected beams is displayed. Probe imaging surface position pixels 601 are coordinates on an ultrasonic image corresponding to the probe imaging surface 501 in FIG. 5. A radiation direction 602 of ultrasonic beams is the direction from the probe imaging surface position pixels 601 to the imaging region 600, and is expressed by a direction vector in the ultrasonic image coordinate system 603.

(Step S304): Imaging Position Obtaining Processing

In step S304, the position and orientation measurement value obtaining unit 1006 obtains information about the position and orientation of the ultrasonic probe 500 which are measured by the position and orientation measurement apparatus 130. The position and orientation measurement value obtaining unit 1006 then executes the processing of generating a transformation matrix from the ultrasonic image coordinate system 603 to the MRI image coordinate system 403 and recording the matrix. Output values from the position and orientation measurement apparatus 130 are the measurement values of the position and orientation of the ultrasonic probe 500 with reference to the coordinate system determined by the position and orientation measurement apparatus 130. In this embodiment in which the position and orientation measurement apparatus 130 includes a magnetic generation unit and a magnetic reception unit, a reference coordinate system is a coordinate system fixed to the magnetic generation unit. It is possible to calculate the position of each pixel of an ultrasonic image in the coordinate system determined by the position and orientation measurement apparatus 130 as a reference by transforming the above measurement values using a known calibration method. For example, associating examination regions commonly depicted in a captured ultrasonic image and an MRI image makes it possible to calculate the relationship between the coordinate system determined by the position and orientation measurement apparatus 130 as a reference and the MRI image coordinate system 403. Performing the above transformation makes it possible to perform transformation from the ultrasonic image coordinate system 603 into the MRI image coordinate system 403. In this embodiment, this transformation is written as a transformation matrix $T_{US\_MRI}$. Calculating equation (1) by using the matrix $T_{US\_MRI}$ can transform a positional coordinate vector $x_{us}$ in the ultrasonic image coordinate system 603 into a positional coordinate vector $x_{MRI}$ corresponding to the MRI image coordinate system 403.

$$x_{MRI} = T_{US\_MRI} x_{US} \quad (1)$$

where $x_{us}$ and $x_{MRI}$ are vectors indicating three-dimensional positional coordinates in the respective coordinate systems, each of which is expressed as an extended four-dimensional vector, and $T_{US\_MRI}$ is a 4-row 4-column matrix expressed by rotation, translation, and scaling.

In step S304 in which the above processing is executed, the position and orientation measurement value obtaining unit 1006 obtains and records the coordinate transformation $T_{US\_MRI}$ which associates the MRI image coordinate system 403 with the ultrasonic image coordinate system 603 captured at the time of measurement by the position and orientation measurement apparatus 130.

(Step S305): Contact Region Detection Processing

Figure 7A:
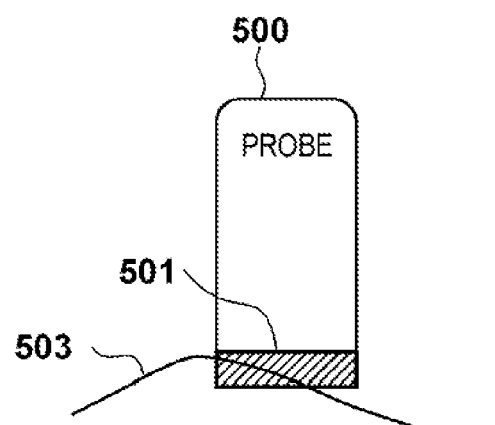
FIGS. 7A to 7C are views for explaining the contact states between an ultrasonic probe and an object to be examined.
Figure 7B:
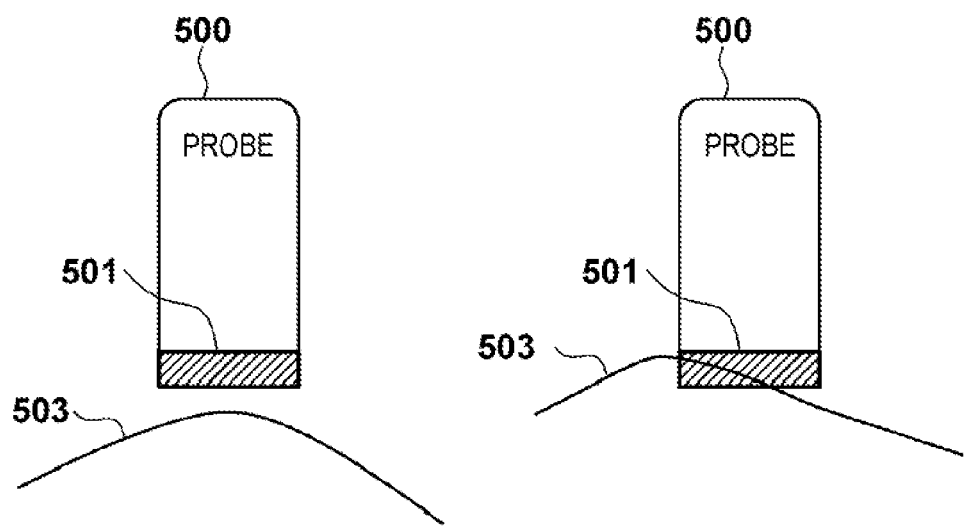
Figure 7C:
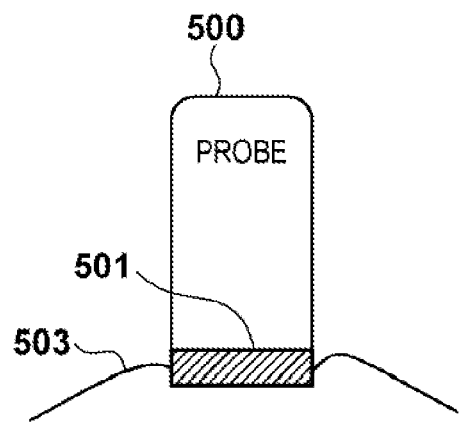
Figure 8A:
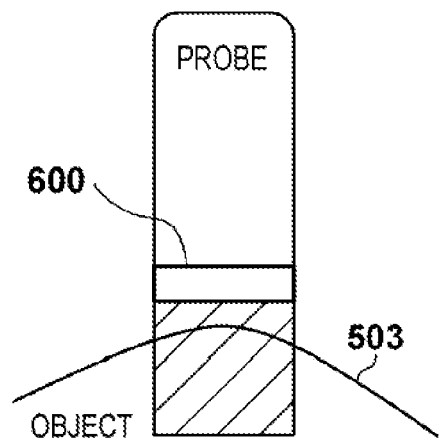
FIGS. 8A to 8C are views for explaining ultrasonic images based on the contact states between the ultrasonic probe and the object.
Figure 8B:
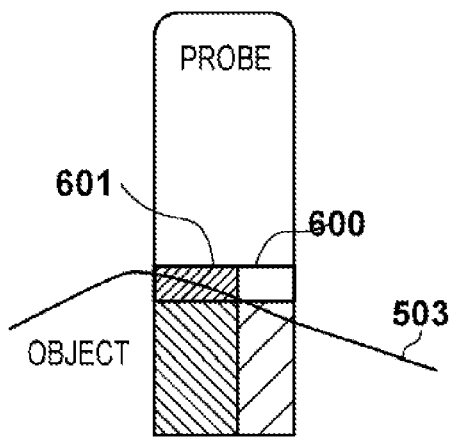
Figure 8C:
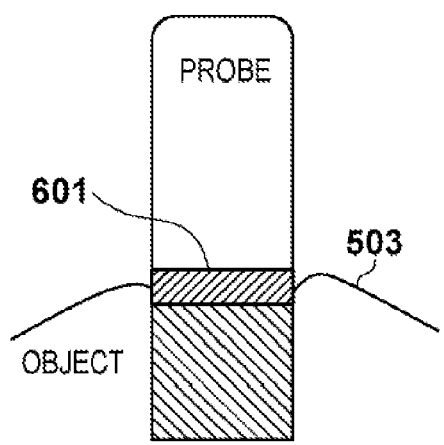

In step S305, the contact state discrimination unit 1004 executes the processing of detecting the contact portion between the probe imaging surface 501 and the surface 503 of the object by processing the obtained ultrasonic image (that is, discriminating a contact portion and a noncontact portion of the object on the probe imaging surface 501). This processing will be described in detail with reference to FIGS. 7A to 7C and 9A to 9C. FIGS. 7A to 7C each show a typical example of the contact state between the probe imaging surface 501 of the ultrasonic probe 500 and the surface 503 of the object. FIG. 7A shows the state in which the overall probe imaging surface 501 is separate from the surface 503 of the object. FIG. 7B shows the state in which part of the probe imaging surface 501 is in contact with the surface 503. FIG. 7C shows the state in which the overall probe imaging surface 501 is in contact with the surface 503. The characteristics of ultrasonic images captured in the respective contact states in FIGS. 7A to 7C will be described next with reference to FIGS. 8A to 8C. FIGS. 8A to 8C are views showing the respective contact states shown in FIGS. 7A to 7C and ultrasonic images captured at the respective times. FIG. 8A shows the state in which the overall probe imaging surface 501 is separate from the surface 503 of the object. In this case, since ultrasonic beams emitted from the ultrasonic probe 500 do not reach the inside of the object, the captured ultrasonic image includes no information about the inside of the object. In this case, the overall luminance value of the B-mode ultrasonic image becomes 0 (black) or a similar value. As shown in FIG. 8B, when part of the probe imaging surface 501 is in contact with the surface 503 of the object, only ultrasonic waves emerging from a portion of the probe imaging surface 501 which is in contact with the surface 503 of the object reach the inside of the object. In this case, only the pixels generated by the ultrasonic beams emerging from the contact portion of the probe imaging surface 501 on the ultrasonic image constitute an image representing the inside of the object, while the luminance values of the remaining pixels become 0 (black) as in the case of the noncontact state. When the overall probe imaging surface 501 is in contact with the surface 503 of the object as shown in FIG. 8C, the entire region of the ultrasonic image becomes an image representing the inside of the object. In step S305, the contact state discrimination unit 1004 determines, by processing the ultrasonic image, whether each of a plurality of ultrasonic beams emerging from the probe imaging surface 501 has reached the inside of the object. The apparatus then estimates the contact state between the probe imaging surface 501 and the surface 503 of the object based on the determination result.

Figure 9A:
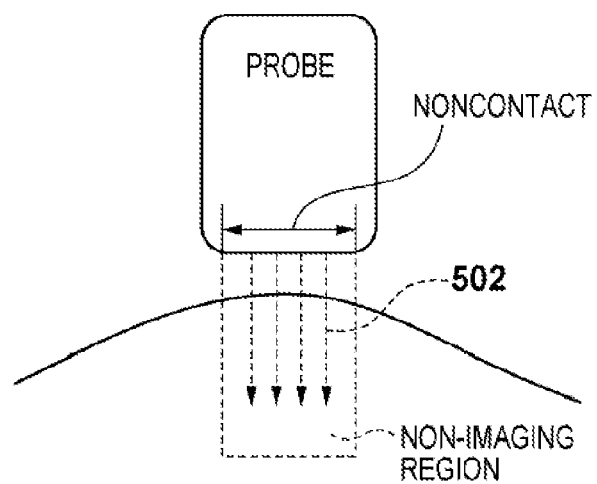
FIGS. 9A to 9C are views for explaining ultrasonic images based on the contact states between the ultrasonic probe and the object in detail.
Figure 9B:
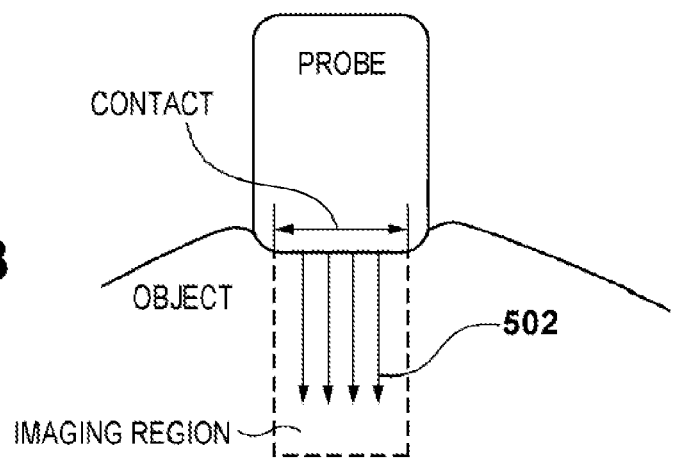
Figure 9C:
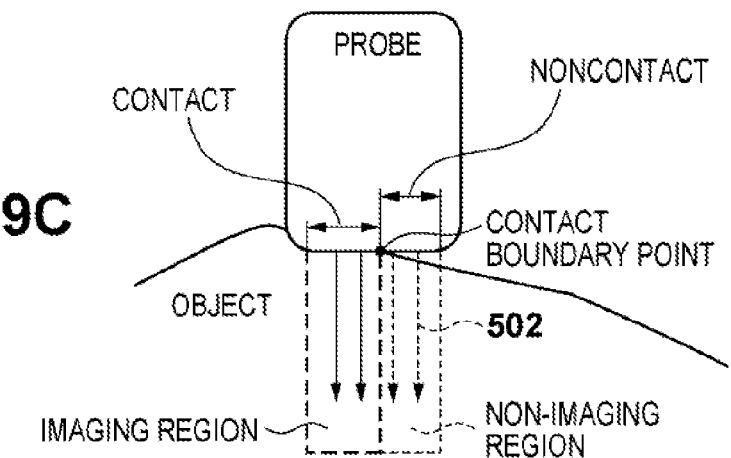

FIGS. 9A to 9C are views for explaining in further detail the patterns of the contact states between the probe imaging surface 501 and the surface 503 shown in FIGS. 7A to 7C, and ultrasonic images captured in the respective states. This embodiment processes a pixel value on a line (scanning line) along which each of the ultrasonic beams 502 propagates to estimate a contact state with the object at the upper end of the scanning line (one point on the probe imaging surface 501). In this estimation, it is possible to switch estimation results depending on whether the average luminance value of pixel values on a scanning line is equal to or more than a predetermined threshold. In this case, if the average luminance value is equal to or more than the predetermined threshold, it can be thought that the ultrasonic wave emitted to image the pixel has reached the inside of the object, and an image obtained by imaging the inside has appeared. It is therefore possible to estimate that the point on the probe imaging surface 501 from which the ultrasonic wave has emerged is in contact with the surface 503. In contrast, if the average luminance value is smaller than the predetermined threshold, it can be thought that the ultrasonic wave emitted to image the pixel has not reached the inside of the object. Therefore, it can be estimated that the point on the probe imaging surface 501 from which the ultrasonic wave has emerged is not in contact with the surface 503 (in a noncontact state). Executing the above processing for all the positions of points constituting the probe imaging surface 501 can estimate whether the probe imaging surface 501 is in contact with the surface 503 of the object at each position. This makes it possible to know the position of each point on the contact boundary between the probe imaging surface 501 and the surface 503 of the object.

Although the above description has been made on the method of estimating contact or noncontact between the probe imaging surface 501 and the surface 503 of the object at a plurality of positions of points constituting the probe imaging surface 501 based on an average luminance value in a predetermined region of an ultrasonic image, the present invention is not limited to this. For example, this apparatus may estimate contact or noncontact based on the magnitude relationship between a predetermined threshold and the variance of luminance values instead of an average luminance value. Other than this, the apparatus may estimate contact or noncontact by, for example, capturing an ultrasonic image in advance in a state in which the probe imaging surface 501 is separate from the surface 503 of the object, calculating a difference image between the ultrasonic image and a currently captured ultrasonic image, and performing estimation based on the difference image. In this case, it is possible to perform estimation by calculating an average luminance value or variance value with respect to the difference image. The present invention is not limited to these methods, and may use any method as long as it can estimate contact or noncontact between each portion of the probe imaging surface 501 and the surface 503 of the object. In addition, the apparatus may estimate contact or noncontact between the probe imaging surface 501 and the surface 503 of the object by using the image obtained by applying a noise removal filter to an ultrasonic image so as to remove the influences of noise and the like mixed in the image. The apparatus may further process the estimated contact/noncontact result so as to suppress variations in estimation result due to the influences of noise and the like. In this case, it is possible to perform the isolated point removal processing of replacing an isolated point different in estimation result from adjacent points with the estimation result on the two adjacent points in the information about contact or noncontact at each point on the probe imaging surface 501. Furthermore, the apparatus may execute a method of determining an estimation result on an isolated point by performing majority processing for estimation results on several adjacent points. With the above methods, the apparatus records information indicating contact or noncontact at each of $N_p$ points $P_j$ ($1 \leq j \leq N_p$) constituting the probe imaging surface 501 as a numerical sequence expressed by equation (2).

$$s_j = \begin{Bmatrix} 0: \text{noncontact} \\ 1: \text{contact} \end{Bmatrix} (1 \leq j \leq N_p) \tag{2}$$

(Step S306): Contact State Determination Processing

In step S306, the alignment mode determination unit 1005 switches the following processes in accordance with the contact state between the probe imaging surface 501 and the surface 503 of the object. That is, if the overall probe imaging surface 501 is separate from the surface 503 of the object, the process advances to step S310. If the overall probe imaging surface 501 is in contact with the surface 503, the process advances to step S307. If a portion of the probe imaging surface 501 is in contact with the surface 503, the process advances to step S308. The apparatus executes this branch processing based on the processing result obtained in step S305. More specifically, if all variables $S_j$ ($1 \leq j \leq N_p$) each recorded as information indicating contact or noncontact with respect to the probe imaging surface 501 and obtained in step S305 are 0 (noncontact), the process advances to step S310. If all the variables $S_j$ ($1 \leq j \leq N_p$) are 1 (contact), the process advances to step S307. In other cases, the process advances to step S308.

(Step S307): Deformation Estimation Processing for Overall Contact

Figure 10A:
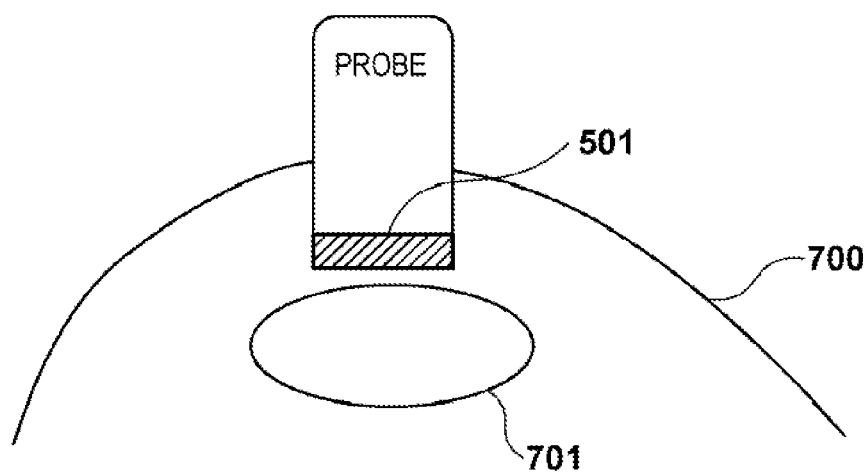
FIGS. 10A and 10B are views for explaining processing in step S307 in FIG. 3.
Figure 10B:
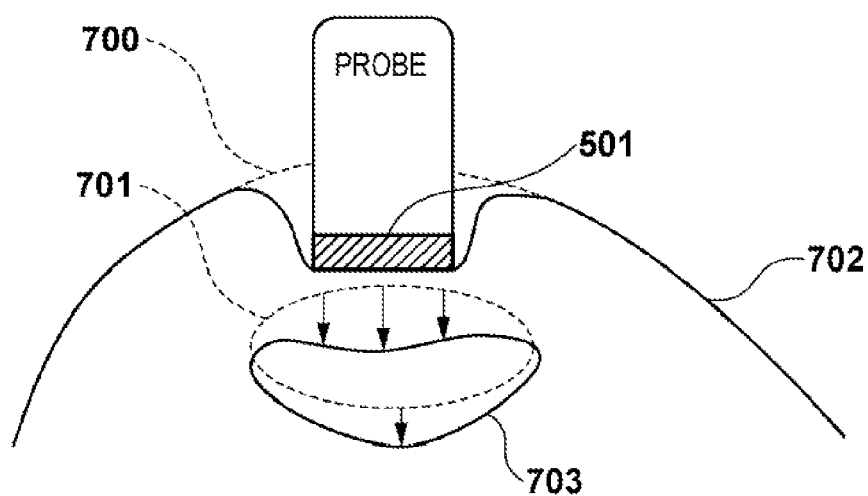

In step S307, the alignment unit 1007 executes deformation estimation processing (alignment processing) so as to match or almost match the shape of the probe imaging surface 501 with that of a surface 700 of the object on the MRI image, as shown in FIGS. 10A and 10B. FIG. 10A shows the positional relationship between the probe imaging surface 501 and the surface 700 of the object at the time of MRI. The processing in step S307 is the one that is executed by the apparatus upon determining that the overall probe imaging surface 501 is in contact with the surface 503 of the object at the time of ultrasonic imaging. For this reason, it is assumed that the probe imaging surface 501 is located more inside the body than the position of the surface 700 of the object at the time of MRI. FIG. 10B is a view for explaining the positional relationship between the probe imaging surface 501 and a surface 702 of the object at the time of ultrasonic imaging. As shown in FIG. 10B, it is assumed that the surface 702 of the object at the time of ultrasonic imaging deforms to the inside more than the surface 700 of the object at the time of MRI because of compression by the ultrasonic probe 500. A portion of the surface 702 matches in position and shape the probe imaging surface 501. In step S307, the apparatus estimates the state of deformation of the object at the time of ultrasonic imaging under the condition that the surface 702 of the object at the time of ultrasonic imaging matches or almost matches in position the probe imaging surface 501. This makes it possible to estimate, in the presence of, for example, a tumor inside the object, variations in position and shape from a tumor 701 at the time of MRI to a tumor 703 at the time of ultrasonic imaging.

A detailed processing procedure in step S307 will be described below with reference to the flowchart of FIG. 11.

Figure 12A:
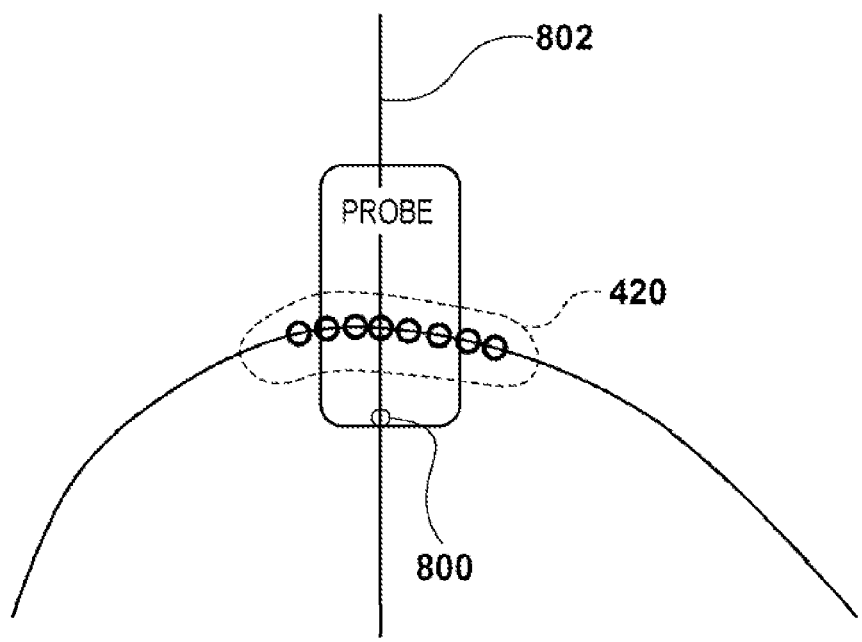
FIGS. 12A and 12B are views for explaining processing in step S3070 in FIG. 11.
Figure 12B:
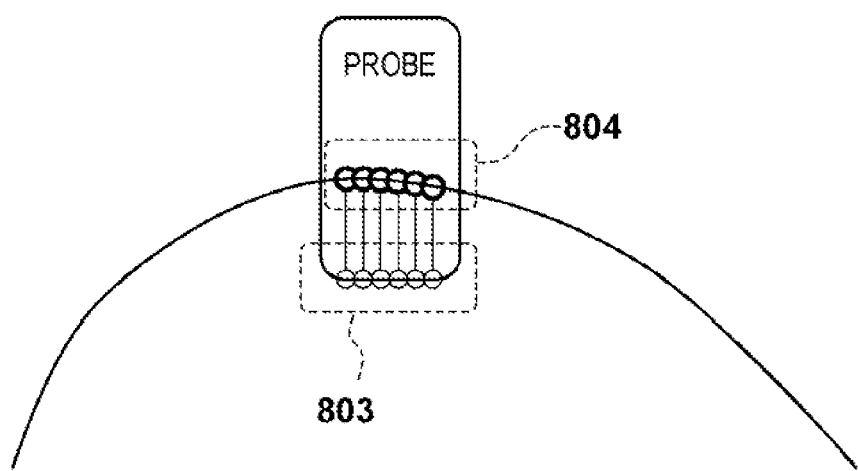

(Step S3070): Association Processing Between Points on Probe Imaging Surface and Surface Points In step S3070, the alignment unit 1007 associates each of $N_p$ points $P_j$ ($1 \leq j \leq N_p$) constituting the probe imaging surface 501 with the surface points 420 (that is, points $S_i$ ($1 \leq i \leq N_s$)) of the object at the time of MRI obtained in step S302. A concrete example of this processing will be described with reference to FIGS. 12A and 12B. Referring to FIG. 12A, a point 800 on the probe imaging surface 501 is an arbitrary point of points $P_j$. Since the coordinates of the point 800 in the ultrasonic image coordinate system 603 are defined as a known value in advance, the coordinates (written as $x_{pj}$) of the point 800 in the MRI image coordinate system 403 can be obtained by transformation using equation (1). A straight line 802 is drawn from the point 800 on the probe imaging surface 501 in the radiation direction of ultrasonic beams, and a point nearest to the straight point is selected from points $S_i$ representing the surface shape of the object. The above processing is executed for each point of the points $P_j$. This makes it possible to obtain points 804 on the surface which are respectively associated with points 803 ($P_j$) on the probe imaging surface 501, as shown in FIG. 12B. In this embodiment, each of the associated points 804 on the surface is written as $C_j$, and its coordinates are written as $x_{cj}$ ($1 \leq j \leq N_p$). These points can be regarded as corresponding points before and after the deformation of the surface of the object due to compression by the probe.

(Step S3071): Deformation Estimation Processing

In step S3071, the alignment unit 1007 executes processing concerning the estimation of the deformation state of the object at the time of ultrasonic imaging based on the positional relationship between the points $P_j$ and the points $C_j$ ($1 \leq j \leq N_p$) associated in step S3070. A concrete example of this processing will be described in detail with reference to FIGS. 13A and 13B.

Figure 13A:
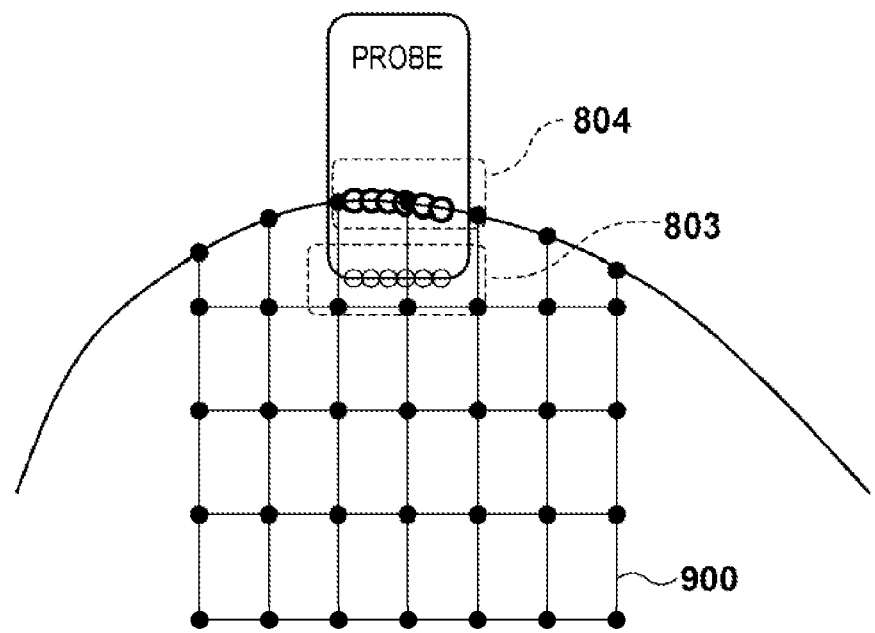
FIGS. 13A and 13B are views for explaining processing in step S3071 in FIG. 11.
Figure 13B:
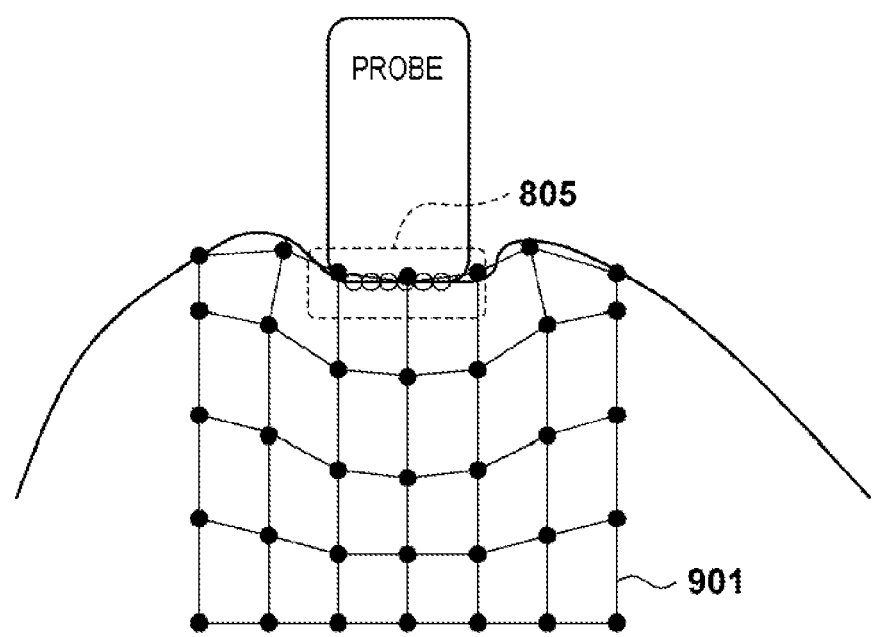

The alignment unit 1007 generates a mesh 900 before deformation like that shown in FIG. 13A in a predetermined region inside the object in the MRI image coordinate system based on the points 803, the points 804, the ultrasonic image capturing range (not shown), and the like. The alignment unit 1007 virtually places this mesh in a region including at least a portion of the surface of the object and a portion of the ultrasonic image capturing range. The region in which the mesh is placed may be, for example, a region extending from the associated points 804 on the surface toward the inside of the object up to a predetermined depth. Other than this, for example, the boundary of an anatomical structure (for example, a bone or muscle) of the object may be extracted from an ultrasonic image, and the boundary may be regarded as an end face of the region. In any case, in this embodiment configured to align a three-dimensional MRI image with an ultrasonic image, the mesh 900 before deformation is generated by arranging elements as three-dimensional structures such as hexahedrons or tetrahedrons in a predetermined three-dimensional region. This mesh can be regarded as being constituted by vertices of these elements. The mesh is used to express the displacement amount of a predetermined region. As the vertices of the mesh are displaced, a predetermined region is displaced accordingly. Based on this, it is possible to obtain the displacements of the associated points 804 on the surface. More specifically, giving a given displacement amount to each of the vertices constituting the mesh 900 before deformation can generate a mesh 901 after deformation as shown in FIG. 13B. It is then possible to specify elements of the mesh 900 which include the respective points 804 and calculate points 805 on the surface after deformation upon displacement of the points 804 based on the position of the vertices of the corresponding elements of the mesh 901 after deformation. This calculation can be executed by applying a known interpolation method such as B-Spline to the set displacement amount of the vertices. In this embodiment, the points 805 after deformation are written as $D_j$, and their coordinates are written as $x_{Dj}$ ($1 \leq j \leq N_p$). The alignment unit 1007 then obtains spatial distances (that is, $\|x_{Dj} - x_{Pj}\|$) between the respective points $D_j$ and the corresponding points $P_j$, and calculates an average value d of the distances. The value d will be referred to as an evaluation function concerning deformation estimation. The displacement amount of each vertex to be given to generate a mesh after deformation is optimized to decrease the value d. That is, the alignment unit 1007 calculates the displacement amount of each vertex of the mesh 900 based on the value d.

Note that a method of optimizing a displacement amount to be given to each vertex can be implemented by a known technique such as the steepest descent method, quasi-Newton's method, or greedy-algorithm. At this time, the displacement amounts of vertices unrelated to the elements including the associated points 804 are indefinite. However, for example, the displacement amounts of such vertices can be set to 0 (fixed). In addition, when obtaining an evaluation function for optimizing the displacement amount of each vertex, it is possible to obtain, for example, the volume change amount or shape change amount of each element based on the displacement of each vertex as well as an amount based on the spatial distance between $D_j$ and $P_j$, and include the obtained values as parts of the evaluation function. More specifically, it is possible to set, as d, the value obtained by adding the average value of spatial distances and the volume change amount and shape change amount of each element with a predetermined weight. This makes it possible to estimate a natural deformation nearer to the reality in a space in which a mesh is placed. In addition, inhibiting the displacement of vertices located the outer ends of the mesh (or fixing them) can prevent unrealistic variations such as the rigid displacement of the overall mesh. In addition, other than the above method of exploratorily deriving the proper displacement of each vertex of a mesh, it is possible to estimate the deformation of a region based on the simulation result obtained by simulating the deformation of the object upon compression by the probe using a technique such as the finite element method. In this case, it is possible to optimize the value d in the same manner as described above by variously changing parameters such as external force concerning the pressing of the probe against the object and the hardness of the inside of the object.

In step S3071, the alignment unit 1007 executes the above processing to calculate the coordinates of vertices constituting the mesh 900 before deformation and the coordinates of vertices constituting the mesh 901 after the deformation and record the coordinates.

As described above, in step S307 in this embodiment, the alignment unit 1007 executes the processing (alignment processing) of estimating the deformation state of the object at the time of ultrasonic imaging under the restriction that the overall probe imaging surface 501 is in contact with the surface 503 of the object.

(Step S308): Deformation Estimation Processing for Partial Contact

In step S308, the alignment unit 1007 executes the processing of deforming the MRI image so as to match or almost match a portion of the probe imaging surface 501 which is in contact with the object with the position of a corresponding surface of the object on the MRI image. FIG. 14A shows the relationship between the position of the probe and the position of the surface of the object. The processing in step S308 is the one that is executed when it is determined that a portion of the probe imaging surface 501 is in contact with the surface of the object. It is estimated that a portion, of the probe imaging surface 501, which is determined to be in contact with the object is located more inside the body than the surface of the object at the time of MRI which is detected in step S302. Likewise, it is estimated that a portion, of the probe imaging surface 501, which is determined to be separate from the object is located more outside the body than the surface of the object at the time of MRI. At this time, as shown in FIG. 14B, it is estimated that the surface shape 702 of the object at the time of ultrasonic imaging deforms to the inside of the object because of compression by the probe. In step S308, the alignment unit 1007 executes the processing (alignment processing) of estimating the deformation state of the object at the time of ultrasonic imaging under the condition that the estimation does not contradict the contact/noncontact state between each portion on the probe imaging surface 501 and the object. With this processing, if a tumor exists inside the object, it is possible to estimate the position and shape of the tumor 703 at the time of ultrasonic imaging from the position and shape of the tumor 701 at the time of MRI.

Figure 15:
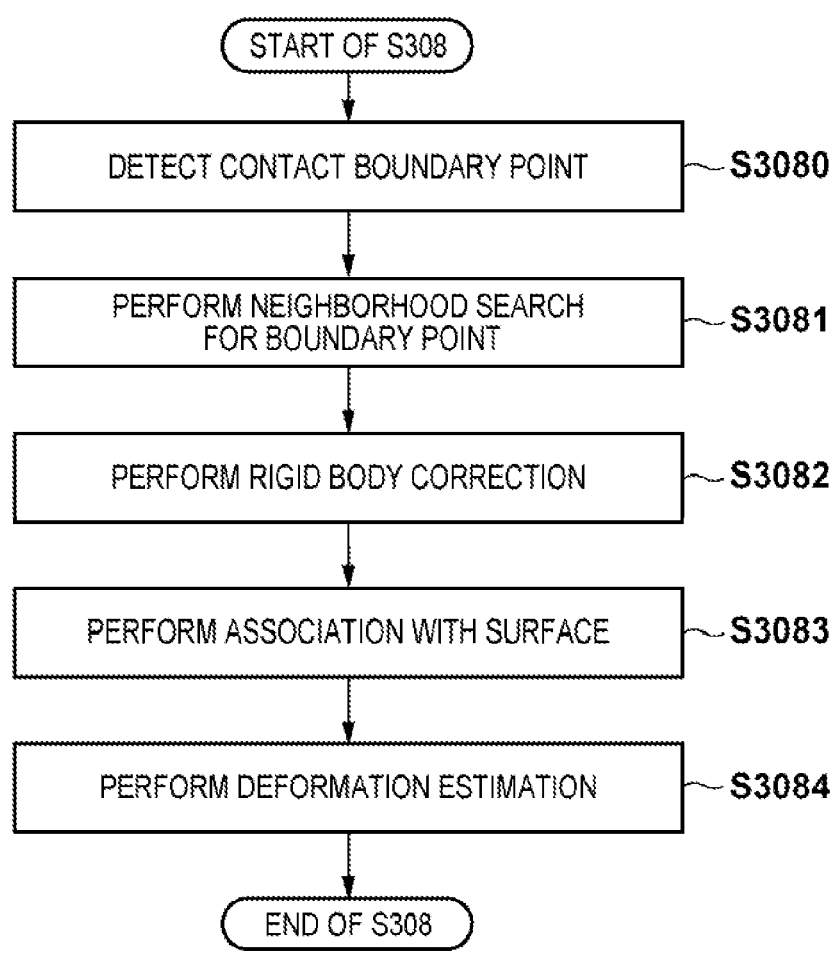
FIG. 15 is a flowchart showing the details of a processing procedure in step S308 in FIG. 3.

A detail processing procedure in step S308 will be described below with reference to the flowchart of FIG. 15.

(Step S3080): Boundary Point Detection Processing

In step S3080, the alignment unit 1007 detects a boundary point at a position where the contact and noncontact states with the object switch on the probe imaging surface 501. The apparatus executes this processing based on the processing result obtained in step S305, that is, contact/noncontact states $S_j$ ($1 \leq j \leq N_p$) of the respective points $P_j$ ($1 \leq j \leq N_p$) constituting the probe imaging surface 501. If, for example, the contact/noncontact state $S_j$ has the relationship given by expression (3), the corresponding portion can be detected as a boundary point.

$$S_j \neq S_{j+1} \qquad (3)$$

The point satisfying the above condition is recorded as a boundary point. A set of such boundary points will be written as $D_k$ ($1 \leq k \leq N_D$). In addition, the coordinates of the points $D_k$ in the MRI image coordinate system are written as $x_{Dk}$ ($1 \leq k \leq N_D$), where $N_D$ represents the number of boundary points. Note that all the points on one side of one point on the probe imaging surface 501 which is a boundary point are in contact with the object, while all the points on the other side are separate from the object, in many situations. Therefore, $N_D = 1$.

(Step S3081): Boundary Point Neighborhood Search Processing

Figure 16A:
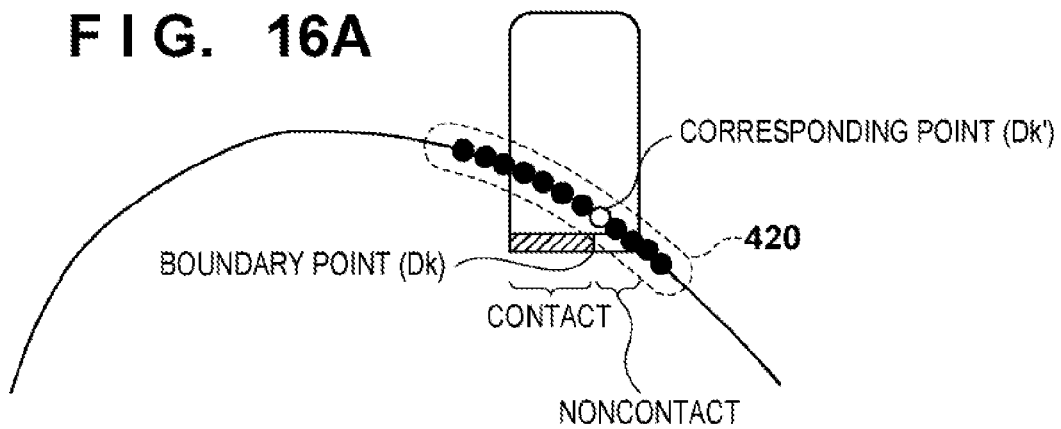
FIGS. 16A to 16C are views for explaining processing in step S3080 in FIG. 15.

In step S3081, the alignment unit 1007 respectively associates the boundary points $D_k$ ($1 \leq k \leq N_D$) with the surface points 420 (that is, the points $S_i$ ($1 \leq k \leq N_s$)) on the object at the time of MRI which are obtained in step S302. As shown in FIG. 16A, the alignment unit 1007 executes this associating operation by executing the processing of selecting a point nearest to each of the points $D_k$ from the points $S_i$. A point associated with each of the boundary points $D_k$ is recorded as $D_k'$, and its coordinates are recorded as $x_{Dk}'$ ($1 \leq k \leq N_D$).

(Step S3082): Rigid Body Correction Processing

In step S3082, the alignment unit 1007 executes the processing of calculating a rigid body transformation matrix $T_{RIGID}'$ that almost matches the boundary points $D_k$ with the corresponding points $D_k'$ based on these points. Multiplying the calculated rigid body transformation matrix $T_{RIGID}'$ will correct a transformation matrix $T_{US\_MRI}$ obtained in step S304.

Figure 16B:
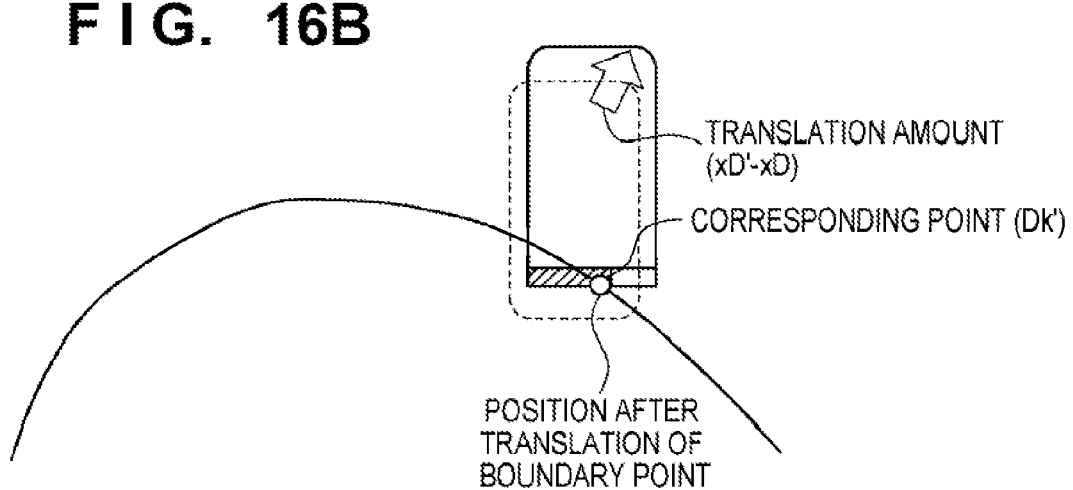

Note that any known method may be used to perform calculation processing for the rigid body matrix $T_{RIGID}'$. As shown in FIG. 16B, if $N_D = 1$, the rigid body transformation matrix $T_{RIGID}'$ can be a rigid body transformation representing translation. For example, expressing a translation amount by $x_{DK}' - x_{DK}$ can obtain a rigid body transformation that matches corresponding points. If $N_D$ is 2 or more, it is possible to perform the above calculation for each of a plurality of points and set the average as a translation amount. In addition, a rigid body transformation including rotation may be obtained based on the positional relationship between the plurality of points.

(Step S3083): Associating Processing with Surface

Figure 16C:
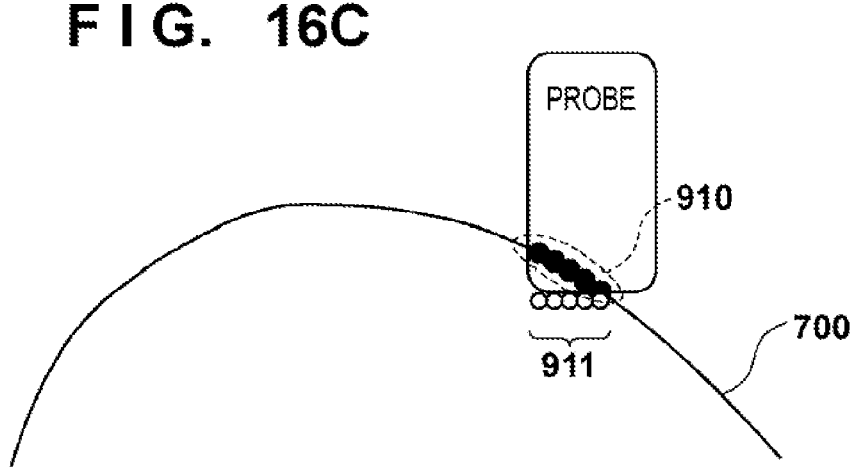

In step S3083, as shown in FIG. 16C, the alignment unit 1007 executes processing similar to that in step S3070 for each of contact points 911 (that is, points $P_j$ ($1 \leq k \leq N_p$) satisfying $S_j=1$) on the probe imaging surface 501 to associate the points with the surface points 420 ($S_i$ ($1 \leq k \leq N_s$)) on the object. Unlike the processing in step S3070, however, the coordinates $x_{pj}$ of the points $P_j$ in the MRI image coordinate system 403 are calculated by using the transformation matrix $T_{US\_MRI}$ after correction in step S3082. With the above processing, the alignment unit 1007 obtains the contact points 911 ($P_j$ ($1 \leq k \leq N_p$, for $S_j=1$)) on the probe imaging surface 501 and points 910 ($C_j$ ($1 \leq k \leq N_p$, for $S_j=1$)) on the surface of the object which are associated with the contact points.

(Step S3084): Deformation Estimation Processing

In step S3084, the alignment unit 1007 executes processing concerning the estimation of the deformation state of the object at the time of ultrasonic imaging based on the positional relationship between the contact points 911 and the corresponding points 910 obtained in step S3082. A concrete example of this processing will be described in detail with reference to FIGS. 17A and 17B.

Figure 17A:
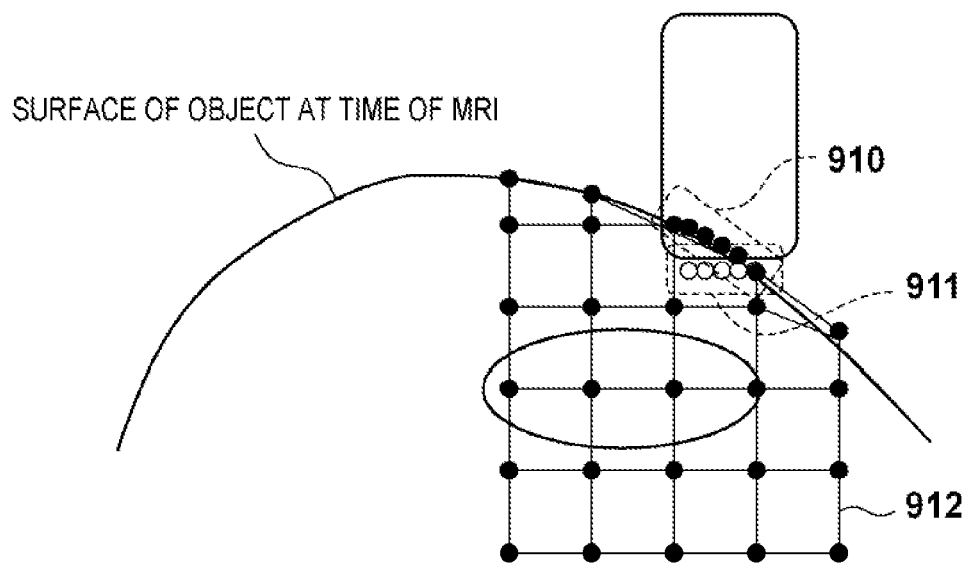
FIGS. 17A and 17B are views for explaining processing in step S3081 in FIG. 15.
Figure 17B:
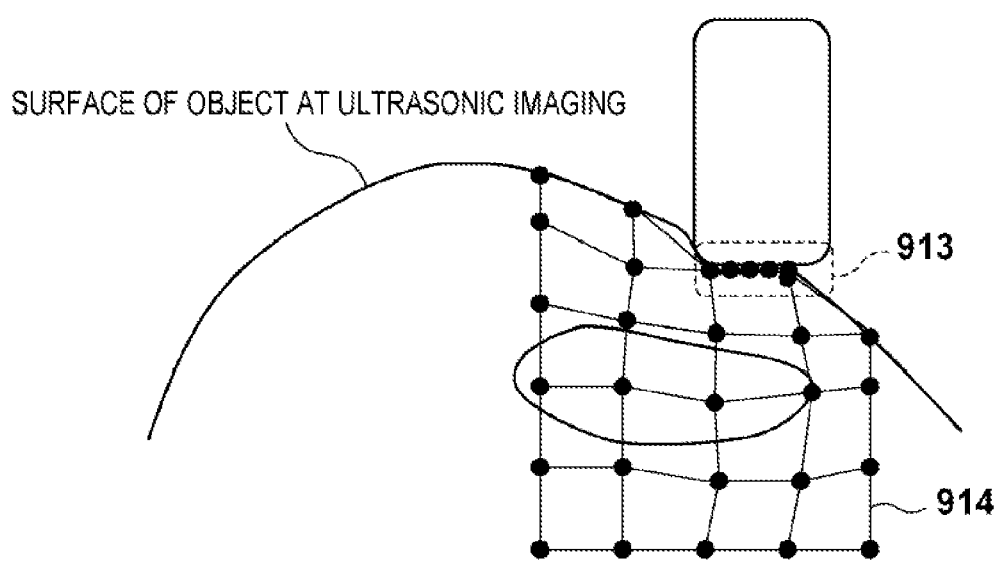

The alignment unit 1007 generates a mesh 912 before deformation like that shown in FIG. 17A in a predetermined region in the object in the MRI image coordinate system. This mesh is determined so as to include at least a portion of the surface of the object at the time of MRI or a portion of an ultrasonic imaging region. In this case, it is possible to calculate a mesh 914 after the deformation like that shown in FIG. 17B by giving proper displacement amounts to the vertices of the mesh 912 before the deformation. At this time, it is possible to calculate the coordinates of the points 913 on the surface after the deformation by displacing corresponding points 910 ($C_j$) based on the displacement amounts given to the vertices of the mesh. This calculation processing can be executed by a method similar to that described in step S3071. The alignment unit 1007 calculates displacement amounts given to the vertices of the mesh by a method similar to that in step S3071 based on the value of an evaluation function d so as to match or almost match the contact points 911 on the probe imaging surface 501 with points 913 on the surface after the deformation.

Methods for the processing performed by the alignment unit 1007 are not limited to these methods. The alignment unit 1007 can calculate displacement amounts given to the vertices of the mesh also based on the relationship between the noncontact portion of the probe imaging surface 501 and the points 913 on the surface after the deformation. In this case, first of all, the alignment unit 1007 obtains points ($E_j$ ($1 \leq j \leq N_p$, for $S_j=0$)), of the points $P_j$ constituting the probe imaging surface 501, which are separate from the object. If the points 913 on the surface of the object after deformation in an assumed deformation state are in contact with the points $E_j$ or located near them, a penalty is applied to the evaluation function d concerning deformation estimation. The alignment unit 1007 then calculates displacement amounts given to the vertices of the mesh based on the value of the evaluation function d in the same manner as described above. This method can estimate a deformation state in consideration of both the contact and noncontact states between the probe imaging surface 501 and the surface of the object at the time of ultrasonic imaging, thereby obtaining an estimation result with higher accuracy.

More specifically, in step S3084, the alignment unit 1007 executes the above processing to execute the processing of calculating the coordinates of vertices constituting the mesh 912 before deformation and constituting the mesh 914 after the deformation and recording the coordinates.

As described above, in step S308, the alignment unit 1007 executes the processing (alignment processing) of estimating the deformation of the object under the restriction that a portion, on the probe imaging surface 501, which is in contact with the surface of the object matches or almost matches the surface of the object after deformation.

(Step S309): Image Generation Processing

In step S309, the deformed image generation unit 1008 executes the processing of generating a deformed MRI image by deforming an MRI image based on the alignment processing result (deformation estimation result) obtained in step S307 or S308. This processing is executed based on the positions of vertices constituting the mesh before the deformation and constituting the mesh after the deformation. More specifically, the deformed image generation unit 1008 generates three-dimensional fields (deformation fields) concerning displacements in regions included in elements constituting a mesh before deformation and constituting a corresponding mesh after the deformation based on the positional relationship between the vertices of the respective elements of the mesh before the deformation and the vertices of the respective elements of the mesh after the deformation. The deformed image generation unit 1008 generates a deformed MRI image based on the deformation fields and the MRI image. At this time, the deformed image generation unit 1008 may generate deformation fields in regions with reference to the mesh before deformation and calculate the positions of the respective pixels of the MRI image upon displacement by using the deformation fields, thereby determining the values of the respective pixels of the deformed MRI image. As another method, the deformed image generation unit 1008 may generate deformation fields in regions with reference to a mesh after deformation and obtain the positions of the pixels of the MRI which is referred to determine the respective pixel values of the deformed MRI image based on the deformation fields.

Although the above description has exemplified the case in which a deformed MRI image is generated by deforming an MRI image. However, the present invention is not limited to this. For example, a deformed ultrasonic image may be generated by deforming an ultrasonic image based on a deformation estimation result. In addition, both a deformed MRI image and a deformed ultrasonic image may be generated.

Furthermore, it is not always necessary to actually generate a deformed MRI image or deformed ultrasonic image. For example, an arrangement configured to generate deformation fields or equivalent information can be an embodiment of the present invention.

(Step S310): Image Display Processing

In step S310, the image display unit 1009 executes the processing of displaying the deformed MRI image generated in step S309 on the monitor 215 of the image processing apparatus 100. If, however, a noncontact state is determined in step S306, since the processing in step S309 is not performed, the image display unit 1009 executes the processing of displaying the MRI image without deformation on the monitor 215. Although various forms of image display are conceivable, it is, for example, possible to generate and display a two-dimensional image by extracting a slice corresponding to a slice which is ultrasonically imaged from a deformed MRI image serving as a three-dimensional image. It is possible to easily obtain a corresponding slice by calculation represented by equation (1). It is possible to use other forms of image display. For example, it is possible to display a two-dimensional image extracted from a deformed MRI image and an ultrasonic image side by side or superimpose and display them.

As described above, the image processing system according to this embodiment can perform alignment between an MRI image and an ultrasonic image with high accuracy at high speed. The most significant feature of this embodiment is that it adaptively executes alignment processing based on the contact state between the ultrasonic probe imaging surface and the surface of an object.

(Modification 1-1): Modification in Case in which there are Plurality of MRI Images The first embodiment has exemplified the case in which an MRI and an ultrasonic image are aligned with each other. However, the present invention is not limited to this. For example, this modification captures two MRI images (first and second MRI images) in advance, and performs proper coordinate transformation for the images in advance as needed. The modification then obtains, with respect to the first MRI image and ultrasonic image, the first MRI image by deforming the first MRI using the method described in the first embodiment. The modification then can obtain the second deformed MRI image by deforming the second MRI image based on the deformation amount obtained in the above processing. According to this processing, the modification has an effect that it can generate the first and second deformed MRI images, which are properly deformed so as to be associated with an ultrasonic image, by efficient processing. This method has an effect that it can perform proper deformation processing for the second MRI image so as to be associated with an ultrasonic image, even if the surface of the object is not depicted on the second MRI image or it is difficult to detect the surface position of the object because of the unclear image or the like.

(Modification 1-2): Modification Using Time-Series Ultrasonic Waves

The first embodiment has exemplified the case in which an MRI image and one ultrasonic image are aligned with each other. However, the present invention is not limited to this. For example, an ultrasonic image may be constituted by a plurality of time-series images, and alignment may be performed for the images by continuous processing. When, for example, aligning an ultrasonic image obtained at the time of execution of processing with an MRI image, it is possible to implement efficient processing by using the result of aligning an ultrasonic image captured in the past by the method described in the first embodiment. More specifically, the alignment result on the past ultrasonic image may be used as an initial value in alignment processing for the current ultrasonic image. According to this method, if consecutive ultrasonic images are similar in imaging position or the deformation state of the object, it is possible to start alignment processing from an initial value near the true value. This can improve the efficiency of the processing in step S307 or S308 in the first embodiment.

In addition, it is not necessary to perform this processing in the forward direction in terms of imaging time. For example, ultrasonic images may be stored in a time-series manner, and the above processing may be performed in the reverse order to which imaging has been performed. Alternatively, it is possible to perform both processing in the forward direction and processing in the backward direction relative to the imaging sequence so as to allow the respective processing results to be compared with each other. This makes it possible to stabilize alignment processing or detect a failure.

In addition, this modification may execute processing based on a three-dimensional ultrasonic image of the object by obtaining and processing ultrasonic images at a plurality of times, accompanied by the movement of the probe. In this case, the modification repeatedly executes the processing from step S303 to step S305 in this embodiment, and stores the processing results. Integrating these processing results can estimate a three-dimensional contact state between the probe imaging surface 501 and the surface 503 of the object and deform an MRI image based on the estimation result. This makes it possible to obtain three-dimensional information concerning the contact between the probe and the object, and hence to perform deformation estimation with higher accuracy.

In addition, the deformation estimation processing may be changed depending on the moving direction of the probe which is calculated during a plurality of times at which ultrasonic images have been captured. For example, this modification may perform deformation estimation based on the moving direction of the probe in consideration of the influence of the frictional force between the probe imaging surface 501 and the surface 503 of the object. When, for example, obtaining a displacement amount to be given to a vertex of a mesh in step S307 or S308, the modification may add a predetermined displacement amount in the same direction as the moving direction of the probe. Other than this, the modification may perform alignment with respect to each of a plurality of times in the same manner as in the first embodiment and obtain a dynamic deformation state transition from the alignment results. The modification may estimate deformation states in adjacent times based on this deformation state transition. For example, it is possible to estimate deformation states in adjacent times by extrapolation based on a deformation state transition in a plurality of times and use the estimation result as an initial value for deformation estimation in the corresponding times. This makes it possible to perform deformation estimation based on the dynamic contact state between the probe and the object, and hence to perform deformation estimation with higher accuracy.

(Modification 1-3): When Ultrasonic Image is Three-Dimensional Image

The first embodiment has exemplified the case in which an ultrasonic image is a two-dimensional tomogram. However, the present invention is not limited to this. For example, the ultrasonic image capturing apparatus 120 may be an apparatus which can obtain a three-dimensional image by ultrasonically imaging an imaging target object. In this case, in step S305, it is possible to detect the three-dimensional contact state between the probe imaging surface 501 and the surface 503 of the object. This makes it possible to estimate the deformation state of the object at the time of ultrasonic image capturing executed in steps S307 and S308 with higher accuracy.

(Modification 1-4): When MRI Image is Combined with Image Other than Ultrasonic Image The first embodiment has exemplified the case in which an MRI image is aligned with an ultrasonic image. However, the present invention is not limited to this. The type of image captured by the medical image capturing apparatus 110 is not limited to MRI images, and may be any images that are captured by imaging the inside of the object and allow to observe the surface shape of the object. In addition, the image captured by the medical image capturing apparatus 110 may not allow to observe the surface shape of the object as long as the image processing apparatus 100 can obtain information obtained by observing the surface shape of the object. It is also possible to use apparatuses which capture other types of images in place of the ultrasonic image capturing apparatus 120. In this case, it is possible to use captured images obtained by an imaging scheme which receives some kind of restriction on the surface of the object. For example, it is possible to use a PAT (Photo Acoustic Tomography) image obtained by imaging the inside of an imaging target object based on the acoustic signal received by the probe, which is generated from the inside of the imaging target object in accordance with a laser beam applied to the imaging target.

(Modification 1-5): When Probe Other than Linear Type is Used

Figure 18A:
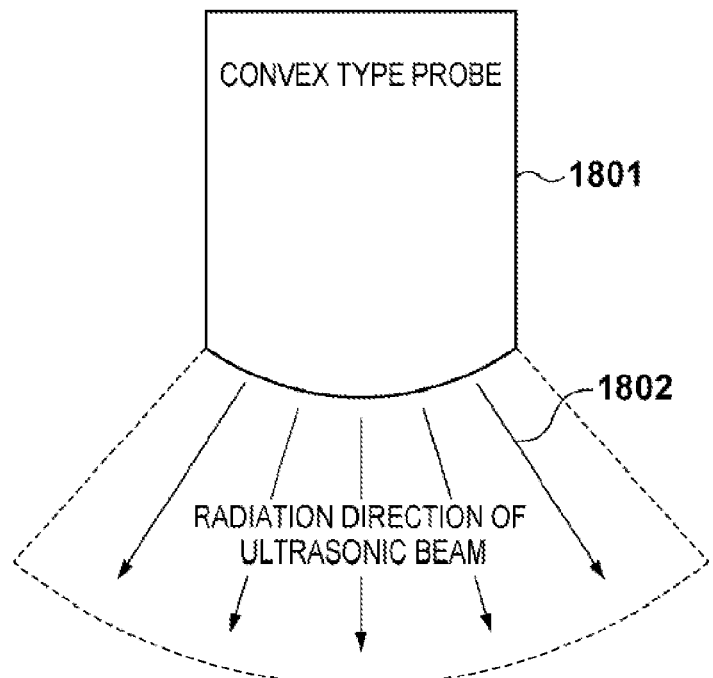
FIGS. 18A and 18B are views for explaining modifications.
Figure 18B:
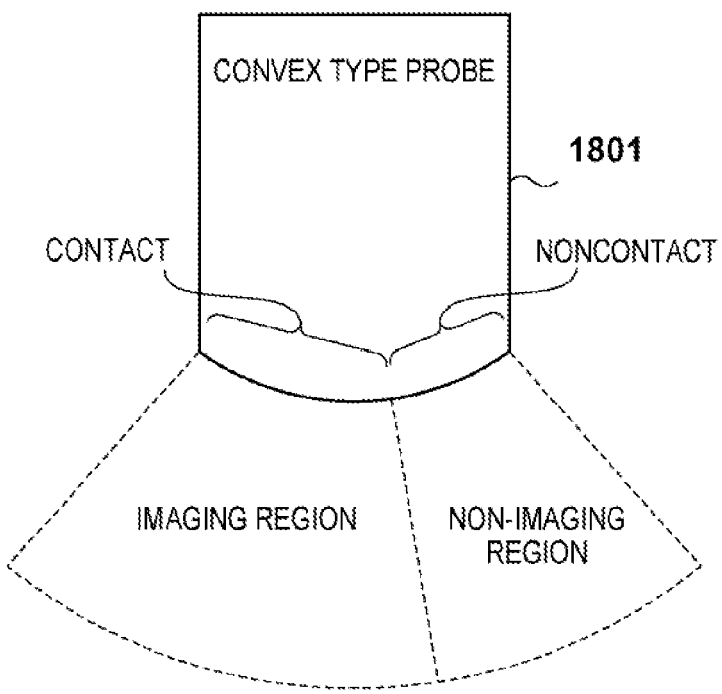

The first embodiment has exemplified the case in which a linear type probe is used as a probe used for ultrasonic imaging. However, the present invention is not limited to this. For example, the probe to be used may be of a convex type or sector type or a probe of any other shape. For example, this modification will be described with reference to the use of a convex type probe. FIG. 18A is a view for explaining a convex type probe and the direction of ultrasonic beams emitted from the probe. As shown in FIG. 18A, a convex type probe 1801 changes the radiation direction for each ultrasonic beam 1802 to be emitted. In this case, processing an ultrasonic image for each line along the ultrasonic beam 1802 emitted from the convex type probe 1801 can detect a contact/noncontact state on the probe imaging surface 501, as shown in FIG. 18B.

(Modification 1-6): When Contact Sensor is Used for Probe

The processing in step S305 in the first embodiment has been described with reference to the case in which the contact state between the probe imaging surface 501 and the surface 503 of the object is estimated based on image processing of an ultrasonic image. However, the present invention is not limited to this. For example, a contact sensor for measuring the contact/noncontact between the probe imaging surface 501 and the object may be attached to the probe imaging surface 501 to obtain the distribution of contact/noncontact states between the probe imaging surface 501 and the surface 503 of the object based on the measurement results obtained by the contact sensor. In addition, the contact sensor to be used may be a sensor which can obtain the distribution of pressures on the probe imaging surface 501 at the time of measurement as well as a sensor which obtains the distribution of contact/noncontact states between the probe imaging surface 501 and the surface 503 of the object. In this case, each of the processes in steps S307 and S308 may also be performed based on the distribution of obtained pressures. For example, in the deformation estimation processing executed in steps S3071 and S3084, estimated pressure values generated on the surface of the object are calculated based on the displacement amounts given to the vertices of the mesh. The evaluation function d may be formed in consideration of the differences between the estimated pressure values and the distribution of pressures measured by the contact sensor. This makes it possible to estimate a deformation at the time of ultrasonic imaging in consideration of the pressures actually generated on the surface of the object, and hence to estimate a deformation state nearer to the reality. Note that a pressure distribution may be calculated based on the transition of deformation estimation results at a plurality of times as well as being measured by the sensor.

(Modification 1-7): When Mesh-Free Deformation Technique is Used

The first embodiment has exemplified the case in which in each of the processes in steps S307 and S308, a virtual mesh is generated in a predetermined region including the surface of the object, and a deformation state is expressed by the displacements of the vertices constituting the mesh. However, the present invention is not limited to this. For example, it is possible to express a displacement field in a predetermined region by using a basis function such as a polynomial. For example, it is possible to generate a displacement field in a predetermined space by placing a radial basis function (RBF) in the space. At this time, this modification can set the center position of the radial basis function and displacement amounts given to the function based on the relationship between the positions of points on the probe imaging surface 501 and the positions of points on the surface which are associated with the points on the probe imaging surface 501. This method does not require the processing of generating a mesh, and hence can express a deformation more simply. Other than this, an arrangement configured to use deformation simulation based on a mesh-free scheme such as a particle method can be embodiment of the present invention.

(Modification 1-8): When Alignment is Performed Also Based on Luminance Values of Images The first embodiment has exemplified the case in which in each of the processes in steps S307 and S308, deformation estimation is performed based on only information about the probe imaging surface 501 and the surface 503 of the object. However, the present invention is not limited to this. For example, in addition to these processes, it is possible to perform deformation estimation based on the luminance values of an MRI image and ultrasonic image. For example, in the processing in step S3071 or S3084, it is possible to calculate the degrees of similarity between the luminance values of an ultrasonic image and those of a deformed MRI image obtained by deforming an MRI image based on an assumed deformation and reflect the degrees of similarity in the deformation evaluation function d. According to this technique, since deformation estimation is based on not only information about the surface of the object but also information of the inside, deformation estimation can be performed with higher accuracy. At this time, it is possible to exclude, from a processing target, a region whose inside cannot be imaged due to the noncontact state between the probe imaging surface 501 and the surface 503 of the object, based on the contact state between the probe imaging surface 501 and the surface 503 of the object. This makes it possible to exclude in advance, from a processing target, an image region which may affect deformation estimation processing, and hence to execute deformation estimation processing more stably.

(Modification 1-9)

The first embodiment has exemplified the case in which in each of the processes in steps S307 and S308, three-dimensional deformation estimation is performed so as to match or almost match the surface 700 of the object on the probe imaging surface 501 with that on an MRI image. However, the present invention is not limited to this. For example, in each of the processes in steps S307 and S308, the deformation of a two-dimensional cross-sectional region including the probe imaging surface 501 may be estimated so as to match or almost match the surface shape of the object on the two-dimensional cross-sectional region with the probe imaging surface 501. In this case, in step S309, only the region corresponding to the cross-sectional region on the MRI image is set as a processing target, and the MRI in the region can be deformed. This method can almost limit the deformation of the object due to the pressure applied from the probe imaging surface 501 to the object to the inside of the cross-section, and hence can obtain a result similar to that in the first embodiment with simpler processing.

Second Embodiment

This embodiment will exemplify a case in which the contact between an ultrasonic probe and an object is determined based on a measurement result on the position and orientation of the ultrasonic probe and the surface shape of the object detected from an MRI image. The arrangement of an image processing system according to the embodiment is the same as that of the image processing system according to the first embodiment, and hence a description of the arrangement will be omitted. The embodiment differs from the first embodiment in the processing executed by a contact state discrimination unit 1004 and an alignment unit 1007.

In step S305, the contact state discrimination unit 1004 detects the contact state between a probe imaging surface 501 and a surface 503 of the object based on information (surface shape information) about the surface of the object which is detected by the surface shape obtaining unit 1002 and the imaging position and orientation of an ultrasonic image which are obtained by a position and orientation measurement value obtaining unit 1006 by position and orientation obtaining processing. That is, the contact state discrimination unit 1004 discriminates the contact and noncontact portions on the probe imaging surface 501 with respect to the object. It is possible to decide whether each of points $P_j$ ($1 \le j \le N_p$) constituting the probe imaging surface 501 described with reference to FIGS. 7A to 7C is in contact with the surface of the object, depending on whether each point is located more inside the body than the surface of the object detected by the surface shape obtaining unit 1002. This makes it possible to execute the processing of estimating the contact state between the probe imaging surface 501 and the surface 503 by processing an ultrasonic image, and hence to reduce the calculation processing load.

In addition, it is possible to execute both the processing of detecting a contact state by using the method according to this embodiment and the processing of detecting a contact state by using the detection method described in the first embodiment. For example, in steps S306 and S308, the alignment unit 1007 can execute processing upon selectively using one of the two detection results obtained by the above methods in accordance with input operation by the user or the like. Other than this, in step S305, this embodiment may determine whether each point on the probe imaging surface 501 is in contact with the surface 503 of the object, depending on the OR or AND of the two results. Furthermore, if the two detection results greatly differ from each other, a warning may be presented to the user to prompt him/her to check them. Other than this, the following processing may be executed. First of all, the embodiment executes steps S306 and S307 or step S308 described in the first embodiment based on one of the two detection results. The embodiment then executes the processing in steps S306 and S307 or step S308 by using the result as an initial value for deformation estimation based on the other detection result. According to these methods which execute both types of processing, it is possible to obtain a desired result more stably even when either of the detection results includes many errors due to the measurement accuracy of a position and orientation measurement apparatus 130, the movement of the object, the image quality of an ultrasonic image, and the like.

Note that the above description of this embodiment is merely an example of a preferred image processing apparatus according to the present invention, and the present invention is not limited to this.

According to the present invention, it is possible to align an ultrasonic image with a three-dimensional medical image with high accuracy at high speed.

Other Embodiments

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (for example, computer-readable storage medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-089536, filed on Apr. 13, 2011, which is hereby incorporated by reference herein in its entirety.

The invention claimed is:
1. An image processing apparatus comprising:
at least a CPU and memory, cooperating to function as:
a shape obtaining unit configured to obtain information indicating a surface shape of a target object;
a determination unit configured to obtain information on a contact region of an imaging surface of an ultrasonic probe, which is in contact with the target object, and a noncontact region of the imaging surface of the ultrasonic probe which captures an ultrasonic image of the target object;
a position and orientation obtaining unit configured to obtain information indicating a position and orientation of the ultrasonic probe at the time of capturing; and
an alignment unit configured to estimate deformation of the target object based on the information indicating the surface shape, the information on the contact region and the noncontact region, and the information indicating the position and orientation, and align the surface shape with an ultrasonic image obtained by using the ultrasonic probe, wherein
the determination unit is configured to obtain the information on the contact region and the noncontact region by determining whether each position in a plurality of positions on the imaging surface of the ultrasonic probe is in a contact state or in a noncontact state at the time of capturing,
the alignment unit is configured to switch an alignment method based on the information on the contact region and the noncontact region which indicates the contact state or the noncontact state for each position of the plurality of positions.

2. The apparatus according to claim 1, further comprising a medical image obtaining unit configured to obtain a medical image of the target object,
   wherein said shape obtaining unit obtains information indicating a surface shape of the target object from the medical image, and
   the alignment unit aligns the medical image including the surface shape with the ultrasonic image.

3. The apparatus according to claim 1, wherein the alignment unit aligns the contact region of the ultrasonic image with a region of the surface shape which corresponds to the contact region.

4. The apparatus according to claim 1, wherein said determination unit determines the contact region or the noncontact region based on whether the ultrasonic image is obtained at each region on an imaging surface of the ultrasonic probe.

5. The apparatus according to claim 1, wherein the determination unit determines the contact region or the noncontact region based on information indicating a position and orientation of the ultrasonic probe and information indicating the surface shape.

6. The apparatus according to claim 1, wherein the determination unit detects a boundary position between the contact region and the noncontact region.

7. The apparatus according to claim 6, wherein the alignment unit performs an alignment based on the boundary position.

8. The apparatus according to claim 1, wherein the alignment unit is configured to switch the alignment method by switching among two or more alignment methods based on the information on the contact region and the noncontact region which indicates the contact state or the noncontact state for each position of the plurality of positions.

9. A method of controlling an image processing apparatus comprising:
   using a CPU,
   obtaining information indicating a surface shape of a target object;
   obtaining information on a contact region and a noncontact region of an imaging surface of an ultrasonic probe between the target object and the imaging surface of the ultrasonic probe which captures an ultrasonic image of the target object;
   obtaining information indicating a position and orientation of the ultrasonic probe at the time of capturing; and
   estimating deformation of the target object based on the information indicating the surface shape, the information on the contact region and the noncontact region, and the information indicating the position and orientation, and aligning the surface shape with an ultrasonic image obtained by using the ultrasonic probe, wherein
   the information on the contact region and the noncontact region is obtained by determining whether each position in a plurality of positions on the imaging surface of the ultrasonic probe is in a contact state or in a noncontact state at the time of capturing, and
   an alignment method is switched based on the information on the contact region and the noncontact region which indicates the contact state or the noncontact state for each position of the plurality of positions.

10. The method according to claim 9, wherein the alignment method is switched by switching among two or more alignment methods based on the information on the contact region and the noncontact region which indicates the contact state or the noncontact state for each position of the plurality of positions.

11. A non-transitory computer-readable storage medium storing a computer program for causing a computer to execute a method of controlling an image processing apparatus comprising:
   obtaining information indicating a surface shape of a target object;
   obtaining information on a contact region and a noncontact region of an imaging surface of an ultrasonic probe between the target object and the imaging surface of the ultrasonic probe which captures an ultrasonic image of the target object;
   obtaining information indicating a position and orientation of the ultrasonic probe at the time of capturing; and
   estimating deformation of the target object based on the information indicating the surface shape, the information on the contact region and the noncontact region, and the information indicating the position and orientation, and aligning the surface shape with an ultrasonic image obtained by using the ultrasonic probe, wherein
   the information on the contact region and the noncontact region is obtained by determining whether each position in a plurality of positions on the imaging surface of the ultrasonic probe is in a contact state or in a noncontact state at the time of capturing, and
   an alignment method is switched based on the information on the contact region and the noncontact region which indicates the contact state or the noncontact state for each position of the plurality of positions.

12. The medium according to claim 11, wherein the alignment method is switched by switching among two or more alignment methods based on the information on the contact region and the noncontact region which indicates the contact state or the noncontact state for each position of the plurality of positions.

13. An image processing apparatus comprising:
   at least a CPU and memory, cooperating to function as:
   a shape obtaining unit configured to obtain information indicating a surface shape of a target object;
   a determination unit configured to obtain information on whether each region on an imaging surface of an ultrasonic probe which captures an ultrasonic image of the target object is in contact with the target object or not;
   a position and orientation obtaining unit configured to obtain information indicating a position and orientation of the ultrasonic probe at the time of capturing; and
   an alignment unit configured to estimate deformation of the target object based on the information indicating the surface shape, the information obtained by the determination unit, and the information indicating the position and orientation, and align the surface shape with an ultrasonic image obtained by using the ultrasonic probe, wherein
   the determination unit is configured to obtain the information by determining whether each position in a plurality of positions on the imaging surface of the ultrasonic probe is in a contact state or in a noncontact state at the time of capturing,
   the alignment unit is configured to switch an alignment method based on the information obtained by the determination unit.

14. The apparatus according to claim 13, wherein the alignment unit is configured to switch the alignment method by switching among two or more alignment methods based on the information on the contact region and the noncontact region which indicates the contact state or the noncontact state for each position of the plurality of positions.

15. An image processing method comprising:
using a CPU,
obtaining first information indicating a surface shape of a target object;
obtaining second information on whether each region on an imaging surface of an ultrasonic probe which captures an ultrasonic image of the target object is in contact with the target object or not;
obtaining third information indicating a position and orientation of the ultrasonic probe at the time of capturing; and
estimating deformation of the target object based on the first information indicating the surface shape, the second information, and the third information indicating the position and orientation, and aligning the surface shape with an ultrasonic image obtained by using the ultrasonic probe, wherein
the second information is obtained by determining whether each position in a plurality of positions on the imaging surface of the ultrasonic probe is in a contact state or in a noncontact state at the time of capturing, and
the estimating step includes switching an alignment method based on the second information.

16. The method according to claim 15, wherein the alignment method is switched by switching among two or more alignment methods based on the information on the contact region and the noncontact region which indicates the contact state or the noncontact state for each position of the plurality of positions.

17. A non-transitory computer-readable storage medium storing a computer program for causing a computer to execute a method of controlling an image processing apparatus comprising:
obtaining first information indicating a surface shape of a target object;
obtaining second information on, for each region on an imaging surface of an ultrasonic probe which captures an ultrasonic image of the target object is in contact with the target object or not;
obtaining third information indicating a position and orientation of the ultrasonic probe at the time of capturing; and
estimating deformation of the target object based on the first information indicating the surface shape, the second information, and the third information indicating the position and orientation, and aligning the surface shape with an ultrasonic image obtained by using the ultrasonic probe, wherein
the second information is obtained by determining whether each position in a plurality of positions on the imaging surface of the ultrasonic probe is in a contact state or in a noncontact state at the time of capturing, and
the estimating step includes switching an alignment method based on the second information.

18. The medium according to claim 17, wherein the alignment method is switched by switching among two or more alignment methods based on the information on the contact region and the noncontact region which indicates the contact state or the noncontact state for each position of the plurality of positions.

19. An apparatus comprising:
at least a CPU and memory, cooperating to function as:
a medical image obtaining unit configured to obtain a medical image of a target object;
a shape obtaining unit configured to obtain information indicating a surface shape of the target object in the medical image;
an ultrasonic image obtaining unit configured to obtain an ultrasonic image generated by capturing the target object with an ultrasonic probe,
a position and orientation obtaining unit configured to obtain information indicating a position and orientation of the ultrasonic probe at the time of capturing; and
an alignment unit configured to obtain information indicating deformation of the target object based on the information indicating the surface shape of the target object in the medical image and the information indicating the position and orientation of the ultrasonic probe, and align at least one of the medical image and the ultrasonic image such that the medical image and the ultrasonic image are aligned based on the information indicating the deformation of the target object,
wherein the alignment unit is configured to obtain information indicating a positional relationship between the surface shape of the target object in the medical image and the ultrasound probe based on the information indicating the surface shape of the target object in the medical image and the information indicating the position and orientation of the ultrasonic probe, and switch an alignment method based on the information indicating the positional relationship.

20. The apparatus according to claim 19, wherein the alignment unit is configured to switch the alignment method by switching a restriction condition for deformation of the target object based on the information indicating the positional relationship.

21. An apparatus comprising:
at least a CPU and memory, cooperating to function as:
a medical image obtaining unit configured to obtain a medical image of a target object;
a shape obtaining unit configured to obtain information indicating a surface shape of the target object from the medical image of the target object;
an ultrasonic image obtaining unit configured to obtain an ultrasonic image generated by capturing the target object with an ultrasonic probe,
a position and orientation obtaining unit configured to obtain information indicating a position and orientation of the ultrasonic probe at the time of capturing; and
a determination unit configured to obtain information on a first region of the ultrasonic probe, which is along the target object, and a second region of the ultrasonic probe, which is a region the ultrasonic probe different from the first region; and
an alignment unit configured to obtain information indicating deformation of the target object based on the information indicating the surface shape of the target object in the medical image, the information on the first region and the second region, and the information indicating the position and orientation, and align at least one of the medical image and the ultrasonic image such that the medical image and the ultrasonic image are aligned based on the information indicating the deformation of the target object,
wherein the alignment unit is configured to switch an alignment method based on the information indicating the first region and the second region.

22. The apparatus according to claim 21, wherein the alignment unit is configured to switch the alignment method by switching a restriction condition for deformation of the target object based on the information indicating the first region and the second region.

* * * * *